(12) United States Patent
Dang et al.

(10) Patent No.: US 10,543,288 B2
(45) Date of Patent: Jan. 28, 2020

(54) MODIFIED-DEXTRANS FOR USE IN OPTICAL GLUCOSE ASSAYS

(71) Applicant: Medtronic MiniMed, Inc., Northridge, CA (US)

(72) Inventors: Tri T. Dang, Winnetka, CA (US); Soren Aasmul, Holte (DK); Jesper Svenning Kristensen, Virum (DK); Joseph Hanna, Burbank, CA (US); Robert McKinlay, Winnetka, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 77 days.

(21) Appl. No.: 15/581,416

(22) Filed: Apr. 28, 2017

(65) Prior Publication Data

US 2018/0311382 A1   Nov. 1, 2018

(51) Int. Cl.
*A61K 49/00* (2006.01)

(52) U.S. Cl.
CPC ................................ *A61K 49/0054* (2013.01)

(58) Field of Classification Search
CPC .. A61K 49/0054; C08L 5/02; G01N 2333/42; G01N 2400/22; G01N 33/542; G01N 33/66; C08B 37/0021
See application file for complete search history.

(56) References Cited

U.S. PATENT DOCUMENTS

| 6,485,703 B1 | 11/2002 | Cote et al. |
| 2013/0060105 A1 | 3/2013 | Shah et al. |
| 2015/0164383 A1 | 6/2015 | Varsavsky et al. |

OTHER PUBLICATIONS

PCT International Search Report & Written Opinion dated Jun. 26, 2018, International Application No. PCT/US2018/029814.
Ballerstadt, Ralph et al., "In Vivo Performance Evaluation of a Transdermal Near-Infrared Fluorescence Resonance Energy Transfer Affinity Sensor for Continuous Glucose Monitoring", Diabetes Technology & Therapeutics, vol. 8, No. 3, 2006, pp. 296-312.
Chaudhary, A. et al., "Evaluation of Glucose Sensitive Affinity Binding Assay Entrapped in Fluorescent Dissolved-Core Alginate Microspheres", Biotechnology and Bioengineering, vol. 104, No. 6, Dec. 15, 2009, pp. 1075-1085.

*Primary Examiner* — Robert S Cabral
(74) *Attorney, Agent, or Firm* — Gates & Cooper LLP

(57) ABSTRACT

The invention is directed to a competitive glucose binding affinity assay comprising a glucose receptor (typically mannan binding lectin) labeled with an assay fluorophore and a modified glucose analog (typically dextran) labeled with a reference fluorophore. In certain embodiments, the glucose analog is dextran and is coupled to both a reference fluorophore and a quencher dye (e.g. hexamethoxy crystalviolet-1). Optionally the reference fluorophore is blue shifted relative to the assay fluorophore.

13 Claims, 27 Drawing Sheets

Filter configuration for AF594-MBL/647-Dex and AF594-MBL/AF647-HMCV1-Dex assays

| | HMCV1 X10 and AF647 X10 5.7/4.1 | | | HMCV1 X5 and AF647 X15 3.6/9.4 | | | HMCV1 X15 and AF647 X5 8.1/2.1 | | |
|---|---|---|---|---|---|---|---|---|---|
| | ASY | REF | Ratio | DR | ASY | REF | Ratio | DR | ASY | REF | Ratio | DR |
| 10:20 | 550 | 215 | 2,56 | 29,4% | 1200 | 225 | 5,33 | 15,4% | 1000 | 300 | 3,33 | 11,0% |
| 10:40 | 308 | 243 | 1,27 | 25,4% | 400 | 450 | 0,89 | 34,1% | 525 | 225 | 2,33 | 18,3% |
| 10:80 | 453 | 297 | 1,52 | 29,3% | | | | | | | | |
| 15:71 | | | | | | | | | | | | |

FIG. 19

MODIFIED-DEXTRANS FOR USE IN OPTICAL GLUCOSE ASSAYS

TECHNICAL FIELD

The invention relates to optical analyte assays, and in particular, fluorescent competitive binding assays for sensing glucose.

BACKGROUND OF THE INVENTION

Maintaining normal glucose levels in vivo is a crucial way that diabetic patients can avoid the long term problems associated with diabetes such as retinopathy, circulatory problems and other sequelae. For this reason, diabetic patients regularly monitor their blood glucose levels to, for example, optimize insulin dosing. In this context, a variety systems and methods have been developed for monitoring blood glucose levels. One strategy detects glucose levels using fluorescent compounds, for example with a competitive binding assay where glucose and fluorophore labeled glucose ligands/analogs compete for the binding site of glucose receptors and the resulting change in fluorescence is translated to a glucose concentration.

In certain competitive glucose binding assays, dextran is used as a displaceable glucose ligand. In such assays, dextran can be labeled with a lipophilic (and cationic) dyes such as hexamethoxy crystal violet-1 (HMCV1). However, the presence of a large number (e.g. greater than 10) of lipophilic dye molecules coupled to the flexible poly-(1,6)-glucose backbone of dextran can cause such labeled dextran molecules to adopt less water soluble conformations, which can result in the precipitation of these molecules. Moreover, such dye-induced conformal changes can drive the labeled dextran into a more lipophilic state, which can cause adverse changes on the binding ability of dextran to the glucose receptor as well as affecting its Förster Resonance Energy Transfer (FRET) efficiency. In addition, in conventional systems, dyes can be shielded intra-molecularly on the dextran, a phenomenon which can result in the calibration of the assay changing over time, thereby introducing instability into the assay.

Reference dyes are also used in certain fluorescence assays in order to track of variations in the experimental setup, e.g. light source fluctuations, changes in the optical path (coupling light into light guides, mechanical perturbations like bending, temperature variations, etc.). Traditionally, optical or fluorescence-based sensing systems have utilized reference fluorophores that are red-shifted relative to the assaying fluorophore. However, by exciting fluorophores using light of a lower wavelength with more energy than needed, there is an increased risk that the electronic transition in the fluorescent molecule will occur from the electronic ground state (S0) to the second excited state (S2) and not to the first excited electronic state (S1). Molecules in S2 are much more likely to decompose than the same molecule in S1. Hence, faster photobleaching occurs if the fluorophores are excited to S2 instead of only S1.

Accordingly, there is a need in the art for optical glucose assays that utilize agents and materials selected to enhance assay stability. The invention disclosed herein meets this need for example, by using assays designed to include multi-labeled glucose analogs/ligands (e.g. dextran coupled/labelled with agents that promote hydrophilicity) and/or blue-shifted reference fluorophores. As discussed below, glucose assays designed to include the multi-labeled glucose analogs and/or blue-shifted reference fluorophores exhibit improvements in material properties such as assay stability.

SUMMARY OF THE INVENTION

The invention provides optimized materials and methods for use in glucose assays. As discussed in detail below, elements in certain fluorescent glucose assays can be selected and/or modified in order to, for example, optimize the hydrophilic-hydrophobic balance of the constellation of elements used to form the assay complex. In doing so, improved assays are generated, ones where fewer undesirable conformal changes to assay elements occur over time. Illustrative modifications to glucose assay complexes include those where dextran is modified by coupling this molecule with agents selected to prevent dextran from becoming unduly negatively or positively charged. Such modifications produce assays that are more stable than their unmodified equivalents. Additionally, in embodiments of where a reference fluorophore is selected for its hydrophilic/hydrophobic profile and/or to be blue-shifted relative to an assay or indicator fluorophore (instead of the typical red-shifted reference fluorophores that can become photo-labile due to low wavelength excitation), the stability of the reference fluorophore and the assay complex as a whole can be increased.

Embodiments of the invention comprise competitive glucose binding affinity assays, and methods for making and using these assays. Typically, the assay comprises a glucose receptor labeled with an assay fluorophore and a glucose analog labeled with both a reference fluorophore and a quencher dye. In embodiments of the invention, the glucose receptor can be selected from the group consisting of mannan binding lectin (MBL), Concanavalin A, glucose galactose binding protein, an antibody, and Boronic acid. In typical embodiments, the glucose receptor is mannan binding lectin. In an illustrative embodiment, the glucose analog is dextran, the assay fluorophore and reference fluorophore are Alexa Fluors™, and the quencher dye is hexamethoxy crystalviolet-1 (HMCV1). In some embodiments, the assay fluorophore and reference fluorophore are individually selected from the group consisting of Alexa Fluor™ 647 (AF647) and Alexa Fluor™ 700 (AF700), and the assay fluorophore and reference fluorophore are different. Typically, in such embodiments, one or more elements of the complex (e.g. dextran) is coupled to or labelled with an agent selected to have a charge and/or hydrophilicity/hydrophobicity profile that contributes to the stability of the agent within the complex and consequently the glucose sensing complex as a whole. Embodiments of the invention also include methods for making and using these improved glucose assays.

In other embodiments of the invention, the assay comprises a glucose receptor labeled with an assay fluorophore and a glucose analog labeled with a reference fluorophore, wherein the reference fluorophore is blue shifted relative to the assay fluorophore. In some embodiments, the glucose analog is further labeled with a quencher dye (e.g. hexamethoxy crystalviolet-1, HMCV1). The glucose receptor may be selected from the group consisting of mannan binding lectin (MBL), Concanavalin A, glucose galactose binding protein, an antibody, and Boronic acid. In one instance, the glucose receptor is mannan binding lectin. Typically, the glucose analog is dextran and the assay fluorophore and reference fluorophore are Alexa Fluors™. Typically, the fluorophore and quencher dye form a Förster Resonance Energy Transfer (FRET) pair. The fluorophore and/or quencher dye is also typically water soluble. In a typical embodiment, the assay fluorophore and reference fluorophore are individually selected from the group consisting of Alexa Fluor 594 (AF594), Alexa Fluor 647 (AF647), and Alexa Fluor 700 (AF700), wherein the reference fluorophore has a shorter wavelength than the assay fluorophore.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Referring now to the drawings in which like reference numbers represent corresponding parts throughout:

FIG. 1A illustrates the quencher being changed from a dye to a fluorophore and omitting the reference fluorophore. FIG. 1B is a graph illustrating the changes in absorbance and emission spectra. FIG. 1C is a graph illustrating glucose concentration measurements and sensor dose response loss (DR loss).

FIG. 2A illustrates the reference fluorophore labeled onto the same ligand as the dye quencher, thereby eliminating the need for a reference carrier. FIG. 2B is a graph illustrating the changes in absorbance and emission spectra. FIG. 2C is a graph illustrating glucose concentration measurements and sensor dose response loss (DR loss).

FIG. 6D is a picture of an explant.

FIG. 7A illustrates the baselines of assay and reference fluorophores. Note the stable assay and reference baselines. FIG. 7B illustrates glucose concentration measurements from Rat study 77.

FIG. 12A is a graph illustrating the normalized absorbance spectra for HMCV1 and AF647. FIG. 12B is a graph illustrating the absorbance spectra of conjugates #478 (HMCV1 X5 and AF647 X15) and #479 (HMCV1 X15 and AF647 X5). FIG. 12C is a graph illustrating conjugate 479 (HMCV1 X15 and AF647 X5) spectra and linear combination of the HMCV1 and AF647 abs spectra. The DOL of MLD conjugates carrying HMCV1 and AF647 include: DOL #472 (X10/X10)=5.7/4.1; DOL #478 (X5/X15)=3.6/9.4; and DOL #479 (X15/X5)=8.1/2.1.

FIG. 19 is a table illustrating that a combination ligand with different DOL values, their DR, and intensity levels in capsule sensors, in accordance with one or more embodiments of the invention.

DETAILED DESCRIPTION OF THE INVENTION

Figure 1A:
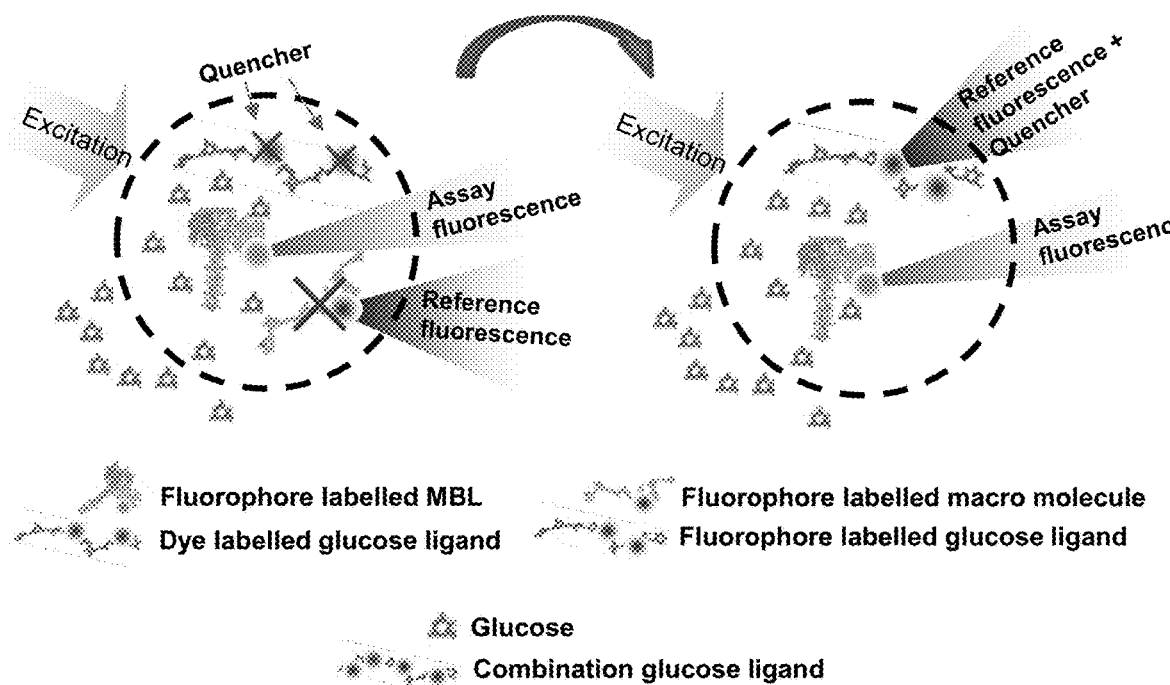
FIGS. 1A-C illustrate a PreciSense™ Optical with a fluorescing ligand, in accordance with one or more embodiments of the invention.
Figure 1B:
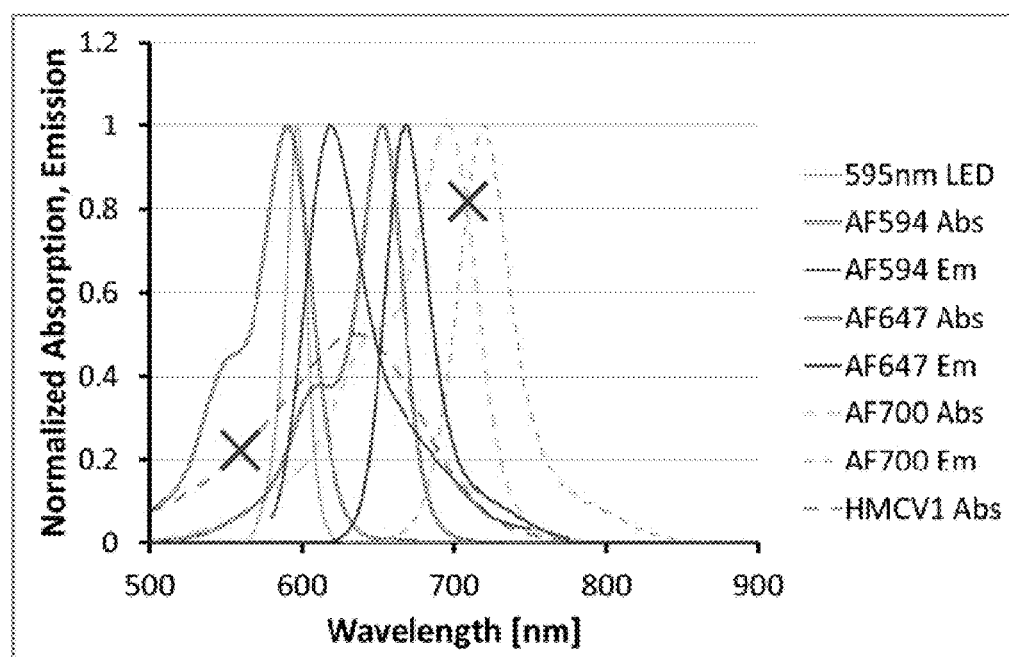
Figure 1C:
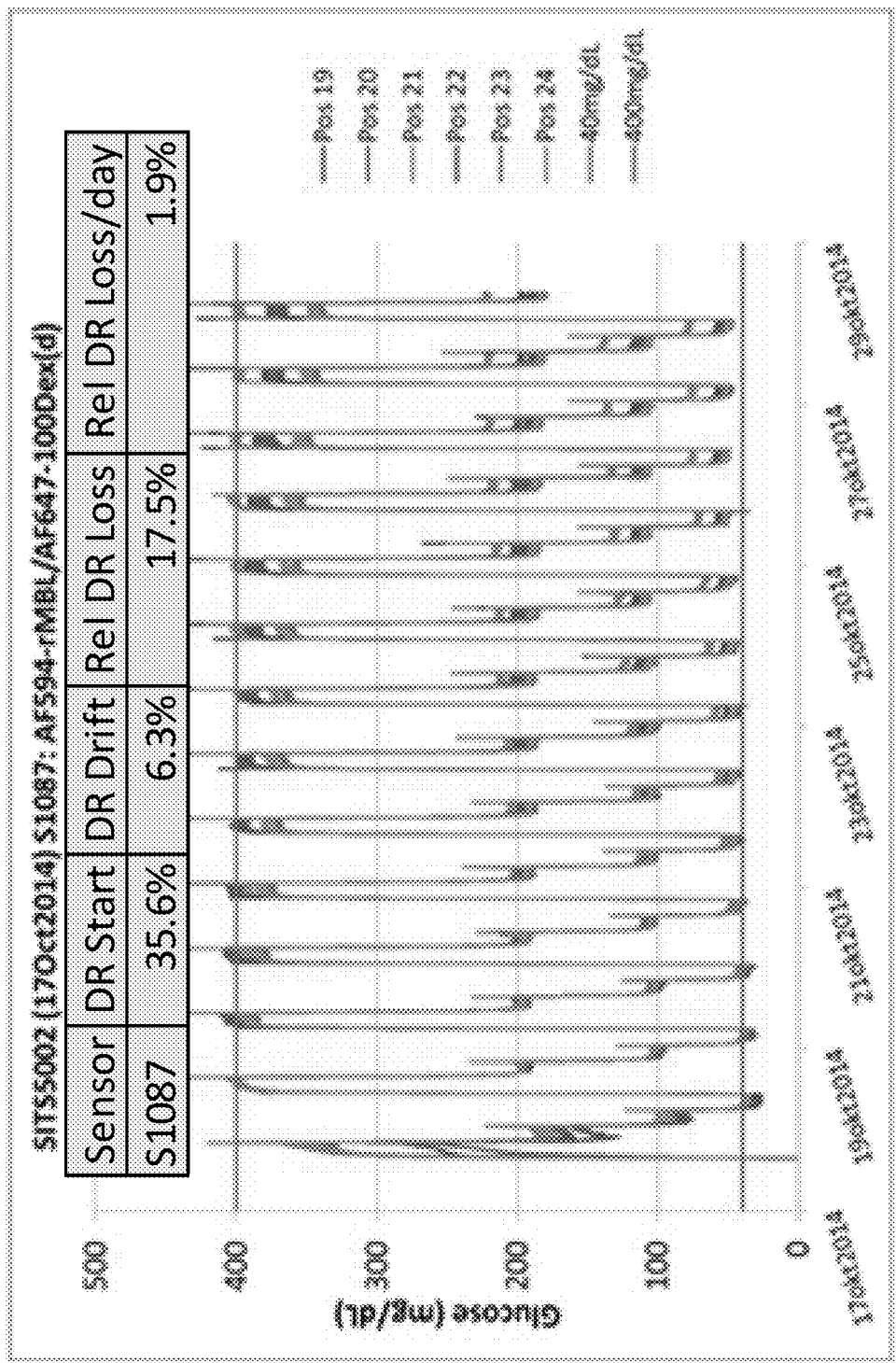

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. All publications, patents, and patent applications cited herein are hereby incorporated by reference in their entirety for all purposes. In the description of a typical embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

Blood glucose is commonly monitored by diabetic patients with the use of commercially available calorimetric test strips or electrochemical biosensors (e.g. enzyme electrodes), both of which require the regular use of a lancet-type instrument to withdraw a suitable amount of blood each time a measurement is made. This imposes a considerable burden on the diabetic patient, both in financial terms and in terms of pain and discomfort, particularly in the long-term diabetic who has to make regular use of a lancet to draw blood from the fingertips. Thus, there have been a number of proposals for glucose measurement techniques that do not require blood to be withdrawn from the patient. It has been observed that the concentration of analytes in subcutaneous fluid correlates with the concentration of said analytes in the blood, and consequently there have been several reports of the use of glucose monitoring devices which are sited in a subcutaneous location. The use of competitive binding assays for glucose which can be remotely interrogated is of particular interest.

A typical method of assaying a competitive binding is to use a proximity-based signal generating/modulating moiety pair (see, e.g. U.S. Pat. No. 6,232,120), which is typically an energy transfer donor-acceptor pair (comprising an energy donor moiety and an energy acceptor moiety). The energy donor moiety is photoluminescent (usually fluorescent). In such methods, an energy transfer donor-acceptor pair is brought into contact with the sample (such as subcutaneous fluid) to be analyzed. The sample is then illuminated and the resultant emission detected. Either the energy donor moiety or the energy acceptor moiety of the donor-acceptor pair is bound to a receptor carrier, while the other part of the donor-acceptor pair (bound to a ligand carrier) and any analyte present compete for binding sites on the receptor carrier. Energy transfer occurs between the donors and the acceptors when they are brought together, which produces a detectable lifetime change (reduction) of the fluorescence of the energy donor moiety. Also, a proportion of the fluorescent signal emitted by the energy donor moiety is quenched. The lifetime change is reduced or even eliminated by the competitive binding of the analyte. Thus, by measuring the apparent luminescence lifetime, for example, by phase-modulation fluorometry or time-resolved fluorometry (see Lakowicz, Principles of Fluorescence Spectroscopy, Plenum Press, 1983, Chapter 3), the amount of analyte in the sample can be determined.

In addition to the lifetime of the excited state, the intensity of the emitted fluorescence also correlates to the glucose concentration. In contrast to a lifetime measurement, the measured intensity of the emitted fluorescence is affected by the intensity of the light source and the coupling between the assay and the optical system. Therefore, the intensity measurement requires an internal reference fluorophore to be incorporated into the assay. The reference fluorophore must differ from the assay fluorophore in a way that the emitted fluorescence from the assay and that from the reference may be separated from one another, e.g., by having different absorption spectra or emission spectra. The reference fluorophore may be, e.g., Alexa Fluor™ 594 (AF594) labeled onto Human Serum Albumin (HSA) or another macro molecule, which largely does not bind to the glucose receptor. Alexa Fluor™ 700 (AF700) may be excited simultaneously with the AF594 as their absorption spectra spectrally overlap. The emission spectrum from AF594 is slightly blue-shifted with respect to AF700, which makes it possible to detect their respective fluorescence emissions in separate wavelength regions. As they are excited simultaneously by the same light source, any changes in the intensity of the light source will scale fluorescence from AF594 and AF700 equally. As such, any effect originating from changes in the intensity of the light source may be canceled out. The excitation, as well as the detection, of the emitted fluorescence for the assay and the reference follow the same optical path from the optical system to the assay. As such, the detected signal from the reference serves as a measure for the optical coupling between the optical interrogating system and the assay. Any effect originating from changes in the optical coupling such as alignment may be canceled out.

A special property of fluorescence known as Förster resonance energy transfer (FRET) occurs when the energy of the excited electron of one fluorophore (i.e. donor), passes onto a nearby acceptor dye, either a quencher (non-emitting chromophore) or another fluorophore, which has an excitation spectrum that overlaps with the emission spectrum of the donor. Energy transfer occurs without the appearance of a photon and is the result of long-range dipole-dipole interactions between the donor and acceptor. An important characteristic of FRET is that it occurs over distances comparable to the dimensions of biological macromolecules. The distance at which FRET is 50% efficient, called the Förster distance, is typically in the range of 20-60 Å. Förster distances ranging from 20 to 90 Å are convenient for competitive binding studies. WO91/09312 describes a subcutaneous method and device that employs an affinity assay based on glucose (incorporating an energy transfer donor-acceptor pair) that is interrogated remotely by optical means. Examples WO1997/19188, WO2000/02048, WO2003/006992 and WO2002/30275 each describe glucose sensing by energy transfer, which produce an optical signal that can be read remotely.

The invention disclosed herein is generally directed towards optical or fluorescence-based assays and analyte sensing compositions. In illustrative embodiments of the invention. the assays, compositions, systems, and methods of the invention are described with reference to glucose as the analyte whose level/concentration is to be determined. However, this is by way of illustration and not limitation, as the principles, devices, systems, and methods of the present invention may be used for sensing and/or determining the level of a variety of other physiological parameters, agents, characteristics, and/or compositions.

As described herein, embodiments of the invention provide sensors designed to include compositions disposed in specific areas of the sensor in order to provide the sensors with enhanced functional and/or material properties. The disclosure further provides methods for making and using such sensors. Embodiments of the invention described herein such as those discussed in the paragraph immediately below can be adapted to and implemented with a wide variety of elements in sensors having sensing complexes that generate an optical signal that can be correlated with the concentration of an analyte such as glucose. A number of these sensors and elements are disclosed, for example in U.S. Pat. Nos. 6,6761,527, 7,228,159, 7,884,338, 7,567,347, 8,305,580 and 8,691,517, and U.S. Patent Application Publication Nos. 2008/0188723, 2009/0221891, 2009/018708, 2009/0131773, 2013/0060105 and 2014/0200336 the contents of each of which are incorporated herein by reference.

The invention disclosed herein have a number of embodiments. An illustrative embodiment is a glucose sensing complex comprising mannan binging ligand coupled to an assay fluorophore, a reference fluorophore (e.g. Alexa Fluor 647 (AF647) or Alexa Fluor 700 (AF700)); dextran that functions in the assay as a glucose analog and is coupled to the reference fluorophore, an agent that enhances the hydrophilicity of the dextran, and a quenching agent (e.g. hexamethoxy crystal violet-1 (HMCV1)). In this embodiment, the assay fluorophore and quenching agent form a Förster Resonance Energy Transfer (FRET) pair. Typically, the fluorophores and/or quencher dye are water soluble. Optionally, the Degree of Labeling (DOL) of the fluorophore is at least 4.1 and the DOL of the quencher dye is at least 5.7. In some embodiments of the invention, the agent that enhances the hydrophilicity of the dextran is the quenching agent. Optionally, the dextran is modified by an anhydride compound (e.g. so as to couple the dextran to a moiety that modulates the hydrophilicity of the dextran). Typically, the dextran comprises less than 1500 glucose units. In some embodiments of the invention, the glucose sensing assay complex exhibits a sensor dose response (DR) loss of less than 2.5% per day.

Embodiments of the invention can comprise a competitive glucose binding affinity assay comprising a glucose receptor labeled with an assay fluorophore, and a glucose analog labeled with both a reference fluorophore (e.g. Alexa Fluor 647 (AF647) or Alexa Fluor 700 (AF700)) and a quencher dye. In certain embodiments of the invention, the glucose receptor is selected from the group consisting of mannan binding lectin (MBL), Concanavalin A, glucose galactose binding protein, an antibody, and Boronic acid, the glucose analog is dextran, the assay fluorophore and reference fluorophore are Alexa Fluors, and the quencher dye is a hexamethoxy crystal violet compound. In typical embodiments, the dextran is coupled to or modified by a compound that enhances its hydrophilicity.

Another embodiment of the method of sensing glucose in a solution (e.g. interstitial fluid or blood) comprising contacting the solution with a glucose sensing complex comprising mannan binging ligand coupled to an assay fluorophore, a reference fluorophore, dextran selected to function in the assay as a glucose analog and which is further coupled to the reference fluorophore. This complex further comprises an agent that enhances the hydrophilicity of the dextran, and a quenching agent. Optionally, the agent that enhances the hydrophilicity of the dextran is the quenching agent. In this embodiment, the assay fluorophore and quenching agent form a Forster Resonance Energy Transfer (FRET) pair. The method includes observing the glucose sensing complex for signals indicative of the presence of glucose, and then correlating observed signals with the concentration of glucose.

Yet another embodiment of the invention is a glucose sensing complex comprising a glucose binding agent (e.g. mannan binding lectin) coupled to an assay fluorophore and a glucose analog coupled to a reference fluorophore. In this embodiment, the reference fluorophore selected for use in this complex is blue shifted relative to the assay fluorophore. Typically, the reference fluorophore has a lower wavelength than the assay fluorophore. Optionally, the assay fluorophore exhibits a wavelength that is at least 50 nanometers greater than the wavelength of the reference fluorophore. Optionally, the glucose analog is further coupled to a quenching agent (e.g. a hexamethoxy crystal violet compound). In certain embodiments, the glucose receptor is selected from the group consisting of mannan binding lectin (MBL), Concanavalin A, glucose galactose binding protein, an antibody, and Boronic acid; and/or the glucose analog is dextran (e.g. dextran having a molecular weight between 90 kDa-110 kDa). In certain embodiments, the assay fluorophore and reference fluorophore are individually selected from the group consisting of Alexa Fluor 594 (AF594), Alexa Fluor 647 (AF647), and Alexa Fluor 700 (AF700). Typically, the reference fluorophore and quencher agent are water soluble, form a Förster Resonance Energy Transfer (FRET) pair.

Another embodiment of the invention is a method of making a glucose sensing complex comprising forming a glucose sensing complex by coupling a glucose binding agent (e.g. mannan binding lectin (MBL)) to an assay fluorophore and coupling a glucose analog (e.g. dextran) to a reference fluorophore. In this embodiment, the reference fluorophore and the assay fluorophore are selected so that reference fluorophore emits light at a wavelength that is blue shifted relative to light emitted by the assay fluorophore. Typically, the assay fluorophore exhibits a wavelength that is at least 50 nanometers greater than the wavelength of the reference fluorophore. Typically, the assay fluorophore exhibits a wavelength that is not more than 100 nanometers from the wavelength of the reference fluorophore. In certain instances, the glucose analog is further treated with succinic acid anhydride. Typically, the dextran is approximately 100 kDa. In certain embodiments, the composition exhibits a sensor dose response (DR) loss of less than 2.5% per day. In one instance, the Degree of Labeling (DOL) of the fluorophore is at least 4.1 and the DOL of the quencher dye is at least 5.7.

Another embodiment of the invention is a method of sensing glucose in a solution (e.g. interstitial fluid or blood) comprising contacting the solution with a glucose sensing complex having a glucose binding agent coupled to an assay fluorophore, and a glucose analog coupled to a reference fluorophore, where the reference fluorophore is selected to be blue shifted relative to the assay fluorophore. This method comprises observing the glucose sensing complex for signals indicative of the presence of glucose, and correlating observed signals with the concentration of glucose. Optionally the method comprises exciting the reference fluorophore and the assay fluorophore with two different light sources. Typically, the assay fluorophore exhibits a wavelength that is not more than 100 nanometers from the wavelength of the reference fluorophore and the assay fluorophore exhibits a wavelength that is at least 50 nanometers greater than the wavelength of the reference fluorophore.

There are a variety of permutations of the invention. As described herein, the analyte receptor is typically a lectin, which includes any carbohydrate-binding protein. In typical embodiments, the glucose receptor is a fluorophore labeled mannan binding lectin (MBL, also called mannose/mannan binding protein, Sheriff et al., Structural Biology, 1:789-794 (1994); Dumestre-Perard et al., Molecular Immunology, 39:465-473 (2002)). Typically, the lectin provides a stable signal in the assay for at least 10 days, more typically for at least 14 days. It is particularly preferable that a stable signal is provided when the sensor is implanted in the human body. Surprisingly, MBL has been found to be stable in a glucose assay for at least 17 days.

Other analyte receptors or analyte binding moieties may be used instead in the assays and sensor systems described herein. For example, the analyte receptor may be a human lectin derived from the human body, including human pulmonary surfactant protein A (SP-A, Allen, et al., Infection and Immunity, 67:4563-4569 (1999)), human pulmonary surfactant protein D (SP-D, Persson et al., The Journal of Biological Chemistry, 265:5755-5760 (1990)) or CL-43 (a human serum protein). Alternatively, the lectin may be a recombinantly manufactured lectin or a humanized animal lectin, for example a humanized bovine lectin. The lectin may alternatively be an animal lectin, bird lectin, fish lectin, vertebrate lectin, invertebrate lectin (e.g. insect lectin) or plant lectin. Suitable animal lectins include conglutinin, collectin-43 (e.g. bovine CL-43), pulmonary surfactant proteins (lung collectins), PC-lectin (US 2003/0216300, US 2004/0265898), CTL-1 (US 2010/179528), Keratinocyte membrane lectins (Parfuemerie and Kosmetik 74, 164-80), CD94 (Eur J Immunol 25, 2433-7), P35 (synonym: human L-ficolin, a group of lectins) (Immunol Lett 67, 109-12), ERGIC-53 (synonym: MR60) (Mol Biol Cell, 7, 483-93), HIP/PAP (Eur J Biochem 267, 1665-71), CLECSF8 (Eur J Immunol 34, 210-20), DCL (group of lectins) (Appl no 00231996/US), and GLUT family proteins, especially GLUT1, GLUT4 and GLUT11 (PNAS 97, 1125-30). Further suitable animal lectins are set out in Appendices A, B, and C of "Handbook of Animal Lectins: Properties and Biomedical Applications", David C. Kilpatrick, Wiley 2000. Suitable plant lectins or phytohemoagglutinins (PHA's) include concanavalin A (Con A) and those derived from *Pisum sativum* (pea), *Lathyrus odoratus* (sweet pea), *Lens culinaris* (lentil), *Narcissus pseudonarcissus* (daffodil), *Vicia faba* (fava bean), and *Vicia sativa* (garden vetch). The analyte receptor may also be a periplasmic glucose/galactose-binding receptor, antibody raised against glucose-like molecules or boronic acid.

As described herein, the analyte analog can comprise a plurality of carbohydrate or carbohydrate mimetic moieties which bind to the binding sites of the analyte receptor. The analyte analogue should have a molecular weight high enough to prevent escape from the sensor but low enough that precipitation does not occur when the analyte analog binds to the analyte receptor. The analyte analog may have a weight in the range of 25 to 250 kDa and more typically between 90 to 120 kDa. In typical embodiments where glucose is the analyte, dextran is used as the displaceable glucose analog/ligand. Dextran is a flexible macromolecule consisting of up to 1500 glucose units. In certain instances, dextran consists of approximately 600 glucose units (~100 kDa), or consists of between 500-700 glucose units.

Other analyte analogs and ligands may be used instead in the illustrative assays and sensor systems described herein. The analyte analog may be a synthetic polymer which bears different carbohydrate or carbohydrate mimetic moieties of different affinity for MBL and similar lectins. Alternatively, the analyte analog may be a carbohydrate-protein conjugate or a carbohydrate-dendrimer conjugate. Examples of suitable carbohydrates for use in such conjugates are monosaccharides and oligosaccharides. Suitable monosaccharides are optionally derivatized tetroses, pentoses, hexoses, heptoses or higher homologous aldoses or ketoses, for example optionally derivatised D-glucose, D-mannose, N-acetyl-D-glucosamine, L-fucose, D-fructose, D-tagatose or D-sorbitol. Suitable oligomers may be linear or branched homooligomers or mixed oligomers, for example containing from 2 to 50 carbohydrate units.

As described herein, fluorophores or fluorochromes are chemical compounds that are able to absorb light energy of a specific wavelength and re-emit light energy at a longer wavelength. Fluorophores can also be used to quench the fluorescence of other fluorescent dyes or to relay their fluorescence at even longer wavelengths (FRET). Typically, Alexa Fluor™ (AF) 594, 647 and/or 700 are used as reference and assay fluorophores for respectively labeling the glucose analog and glucose receptor. Those skilled in the art understand that other fluorophores suitable for optical glucose assays may also be used instead, for example, coumarin, rhodamine, xanthene, cyanine, and Alexa Fluor dyes that cover other excitation and emission wavelengths (e.g. AF350, AF405, AF488, AF532, AF546, AF555, AF568, AF594, AF680, AF750).

An energy acceptor which does not emit fluorescence is referred to as a quenching moiety. The HMCV dyes described in WO05/059037 are suitable energy acceptor moieties for use in the invention. These dyes are stabilized carbenium ions. In typical embodiments, hexamethoxy crystal violet-1 (HMCV1) is used as the quencher/acceptor dye. Alternatively, QSY 21 may be used as an energy acceptor moiety with AF594 as an energy donor moiety.

The binding assay generating the optical signal should typically be reversible such that a continuous monitoring of fluctuating levels of analyte can be achieved. This reversibility is a particular advantage of the use of a binding assay format in which the components of the assay are not consumed. Typically, the sensor is suitable for the detection or measurement of glucose in body fluid, for example subcutaneous fluid. It is desirable for the sensor to be suitable for use in vivo. Typically, the assay is capable of measuring blood glucose for concentrations over at least part of the range of 0 to 35 mM glucose, typically over the range of 2 to 10 mM glucose. Suitable detection techniques include FRET, fluorescence energy transfer, fluorescence polarization, fluorescence quenching, phosphorescence, luminescence enhancement, luminescence quenching, diffraction or plasmon resonance. Typically, the sensor of the invention incorporates an assay which generates an optical readout using the technique of FRET.

As discussed above, there is a need in the art for optical or fluorescence-based assays with enhanced stability and that require a lower calibration frequency of the optical sensor. In one aspect of the invention, an analyte sensing composition with significantly improved stability and solubility is provided. The analyte sensing composition comprises an analyte analog labeled with both a fluorophore and a quencher dye. In typical embodiments, the analyte sensing composition is a glucose sensing composition comprising a multi-labeled glucose analog (e.g. dextran) labeled with both a fluorophore (e.g. Alexa Fluor™ 647, Alexa Fluor™ 700) and a quencher dye (e.g. hexamethoxy crystal violet-1, HMCV1).

In another aspect of the invention, a competitive analyte binding affinity assay based on the analyte sensing composition is provided. The competitive analyte binding affinity assay comprises an analyte receptor labeled with an assay fluorophore and an analyte analog labeled with both a reference fluorophore and a quencher dye. In certain instances, the reference fluorophore is blue-shifted relative to the assay or indicator fluorophore, which improves the stability of the assay, and more specifically the reference fluorophore. In typical embodiments, the competitive analyte binding affinity assay is a competitive glucose binding affinity assay comprising a glucose receptor/lectin (e.g. mannan binding lectin, MBL) labeled with an assay fluorophore (Alexa Fluor™ 647, AF647) and a multi-labeled glucose analog (e.g. dextran) labeled with both a reference fluorophore (e.g. Alexa Fluor™ 594, AF594) and a quencher dye (e.g. HMCV1).

In embodiments of the invention, the binding between the MBL and glucose-like molecules (e.g., dextran) is reversible. When no glucose is present, MBL and dextran will predominantly be bound together. When glucose is added to the assay, it will compete off a part of the dextran population, such that the assay enters a new equilibrium state. The equilibrium state at all times corresponds to the glucose concentration. In order to determine this equilibrium state, MBL is labeled with a fluorophore (e.g. AF647, AF700) and the dextran is multi-labeled with a quencher dye (e.g. HMCV1) and a reference fluorophore (e.g. AF594). The donor assay fluorophore and the acceptor quencher dye together form a Förster Resonance Energy Transfer (FRET) pair—i.e., the emission spectrum of the assay fluorophore and the absorption spectrum of the quencher dye overlap. It is noted that the fluorophore and dye are typically water soluble, as they are to function in an aqueous environment.

Multi-Labeled Analyte Analogs

Embodiments of the invention include glucose assay complexes comprising dextran as a glucose analog. Dextran is a flexible macromolecule made up of up to 1500 glucose units. In certain typical instances, dextran is made up of approximately 600 glucose units (~100 kDa). Dextran may be used as a displaceable analyte analog/ligand in an optical mannan binding lectin (MBL)-based glucose responding competitive assay. In order to function in the Förster Resonance Energy Transfer (FRET) assay, dextran is typically (heavily) labeled with a lipophilic (and cationic) dye such as hexamethoxy crystal violet-1 (HMCV1). The presence of a large number (greater than 10) of lipophilic dyes on the flexible poly-(1,6)-glucose backbone of dextran can cause the HMCV1-labeled dextran to fold to less soluble conformations and hence create precipitations. Dye-induced conformal changes turn the HMCV1-labeled dextran into a more lipophilic state which causes various problems, including adverse changes on the binding ability of dextran to the glucose receptor as well as affecting its Förster Resonance Energy Transfer (FRET) efficiency. An inner filter effect also occurs due to the dyes being shielded intra-molecularly on the dextran, which causes the calibration of the assay to change, i.e. during this process the assay behaves unstably.

In one aspect of the invention, dextran is co-substituted with a typical quencher (e.g. HMCV1) together with dyes or other components having a more hydrophilic character, which allows for a better hydrophilic-hydrophobic balance where less conformal changes to the glucose ligand/analog over time occurs. The co-substitution can also comprise of positive and negative charged substitutes which prevent dextran from becoming fully negative or positive. Illustrative experiments have shown that these factors allow for a significantly more stable assay for the optical sensor.

In one embodiment, as shown in FIG. 1A, the quencher is changed from a dye to a fluorophore and the reference fluorophore is omitted. This improves the stability of the assay by improving the solubility of the ligand. It also reduces complexity of the assay as the AF647-labeled dextran acts as both an acceptor and a reference at the same time. Additionally, this improves the photo stability of the assay by exciting the reference fluorophore. In this context, blue shifting the reference fluorophore towards the excitation source will prevent fluorophore excitation to the second excited state, a phenomenon which can lead to dye degradation. By shifting the dye towards the light source excitation wave length we can obtain less photo bleaching (UV light bleaches visible dyes more than visible light). Blue shifted reference dyes useful in embodiments of the invention (depending on, for example, the excitation filter and the wavelength width of the light source) include Alexa Fluor (AF) 546, AF555, AF568, AF594 and Cy3, Cy3B and Cy3.5. These are the blue shifted reference dyes compatible with the AF647 donor and HMCV1 acceptor FRET system.

A variety of other agents can be coupled to dextran to improve its conformation and/or hydrophilic-hydrophobic balance, typically to enhance hydrophilicity. Illustrative agents include cyclic anhydrides (e.g. Phthalic anhydride), Tartraic anhydride derivates (e.g. O,O-Diacetyl-L-tartaric anhydride), and the agents shown in Table 1 below:

| n | Common name | IUPAC name | Structure | $pK_a1$ | $pK_a2$ |
|---|---|---|---|---|---|
| 2 | Succinic acid | butanedioic acid | 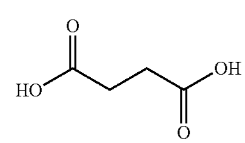 | 4.21 | 5.41 |
| 3 | Glutanic acid | pentanedioic acid | 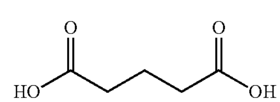 | 4.34 | 5.41 |
| 4 | Adipic acid | hexanedioic acid | 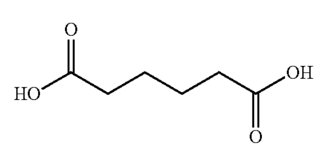 | 4.41 | 5.41 |
| 5 | Pimelic acid | heptanedioic acid | 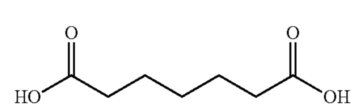 [SMILES: O=C(O)CCCCCC(=O)O] | 4.50 | 5.43 |

-continued

| n | Common name | IUPAC name | Structure | pk$_a$1 | pK$_a$2 |
|---|---|---|---|---|---|
| 6 | Suberic acid | octanedioic acid | HO-(CH$_2$)$_6$-COOH (octanedioic acid structure) | 4.526 | 5.498 |
| 7 | Azelaic acid | nonanedioic acid | HO-(CH$_2$)$_7$-COOH (nonanedioic acid structure) | 4.550 | 5.498 |
| 8 | Sebacic acid | decanedioic acid | HO-(CH$_2$)$_8$-COOH (decanedioic acid structure) | | |

Figure 2A:
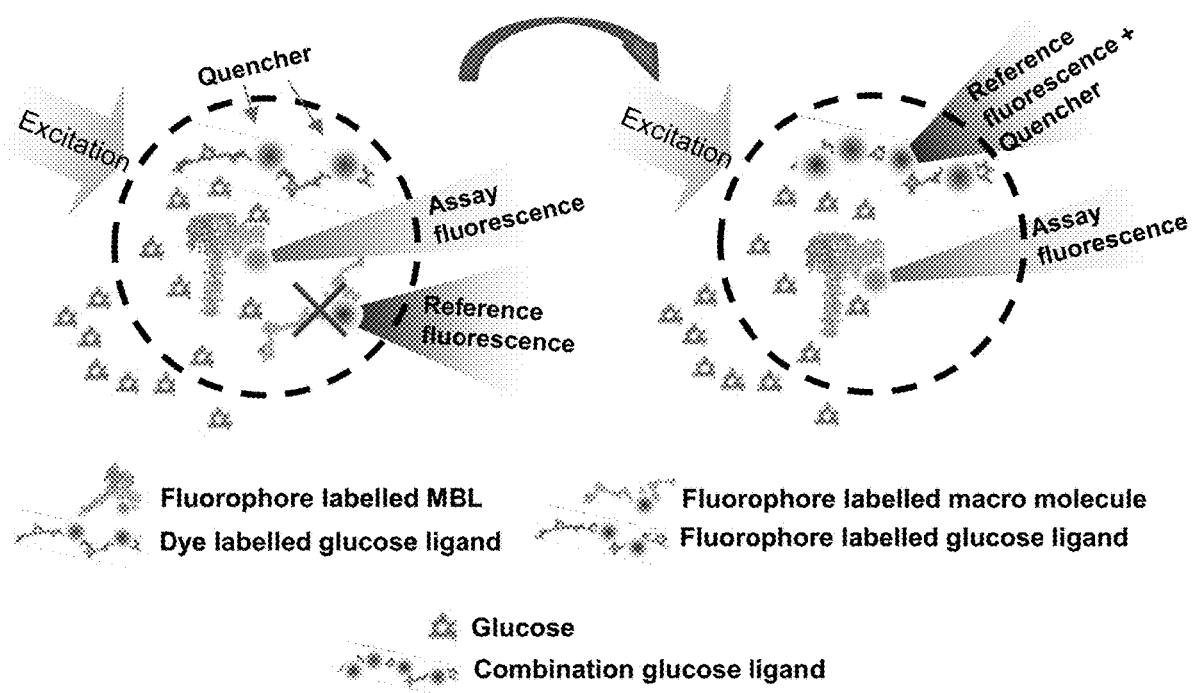
FIGS. 2A-C illustrate a PreciSense™ Optical with a combination ligand, in accordance with one or more embodiments of the invention.
Figure 2B:
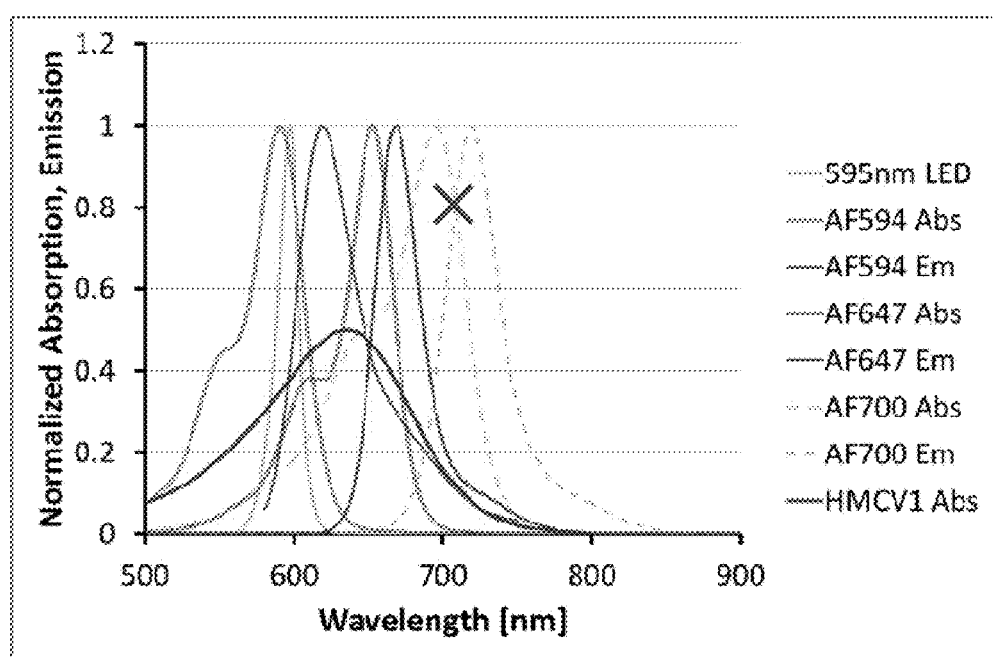
Figure 2C:
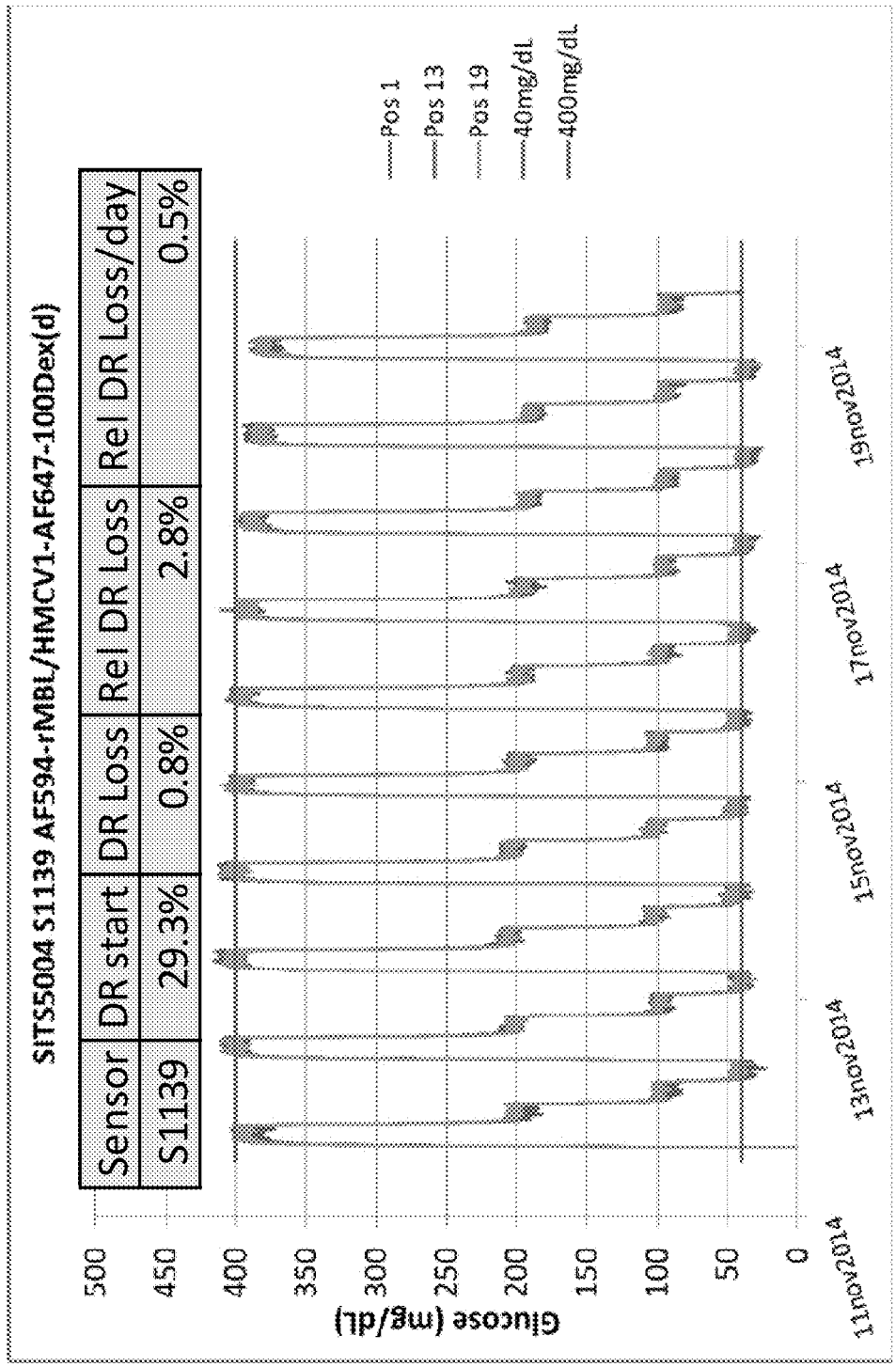
Figure 3:
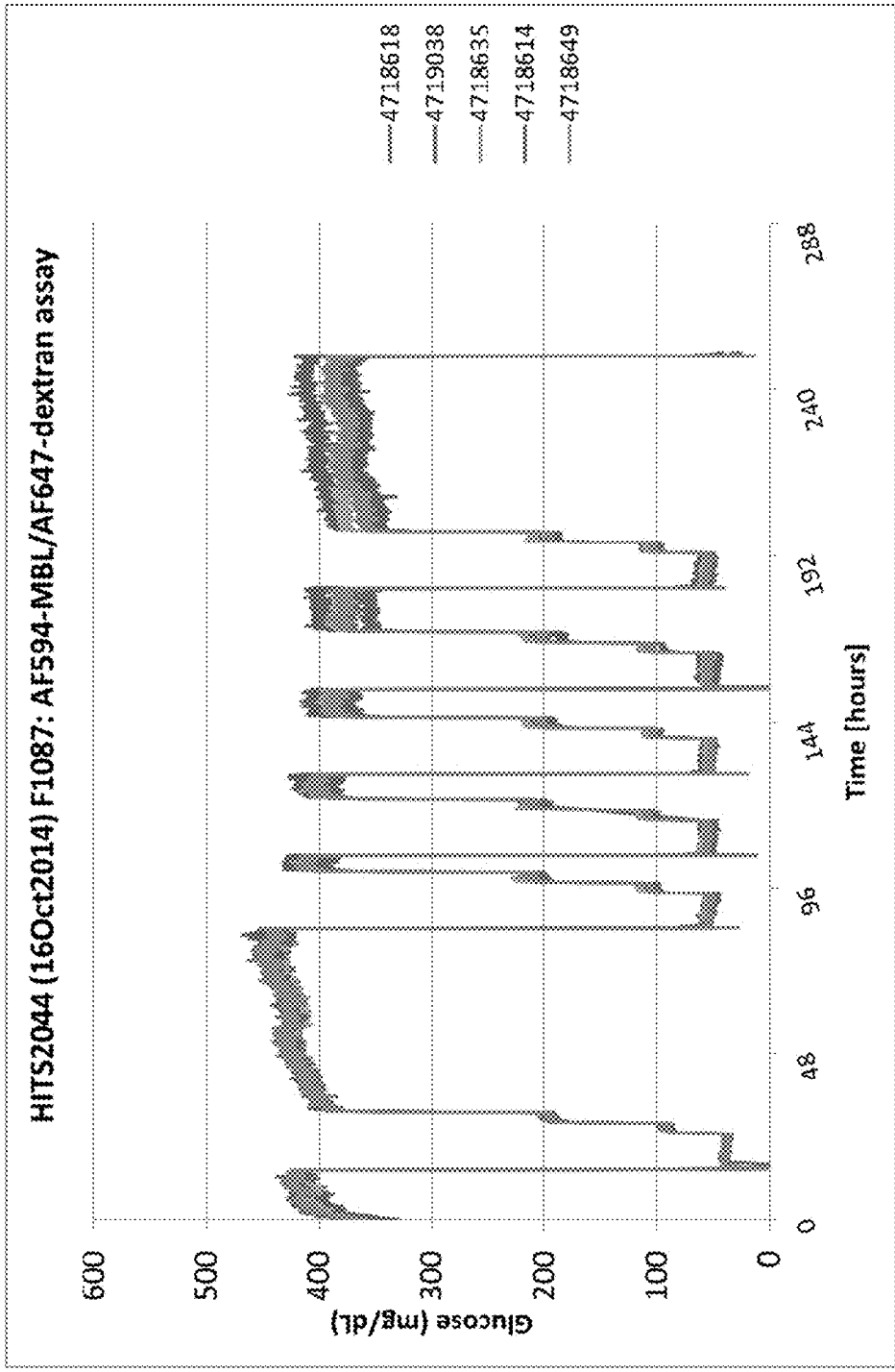
FIG. 3 is a graph illustrating ORS SITS data for an AF594-MBL/AF647-dex assay, in accordance with one or more embodiments of the invention.
Figure 4:
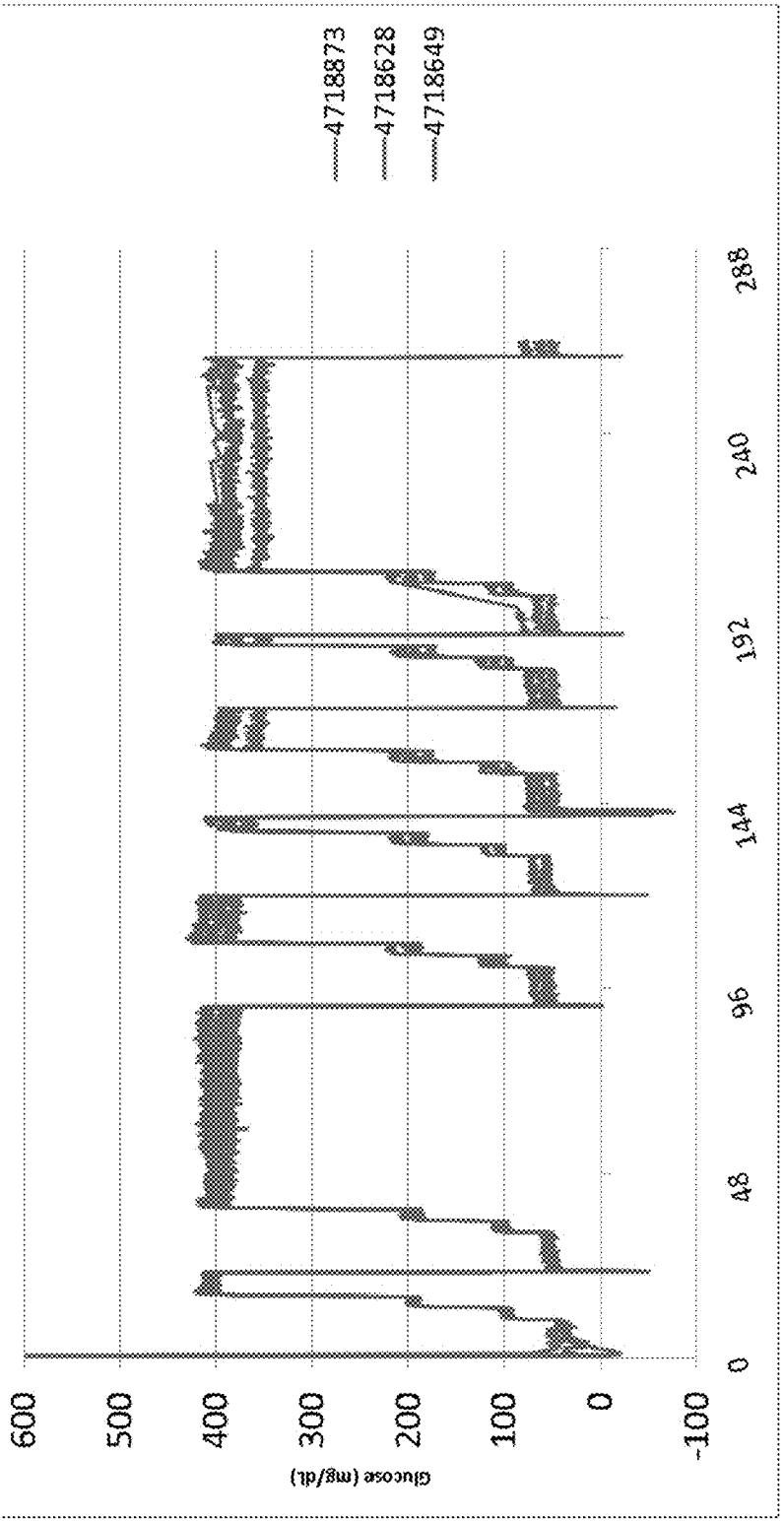
FIG. 4 is a graph illustrating ORS SITS data for an AF594-MBL/AF647-HMCV1-dex assay, in accordance with one or more embodiments of the invention. The same is used for Rat trial 76 and 77 as shown in FIGS. 5-7 below.
Figure 5:
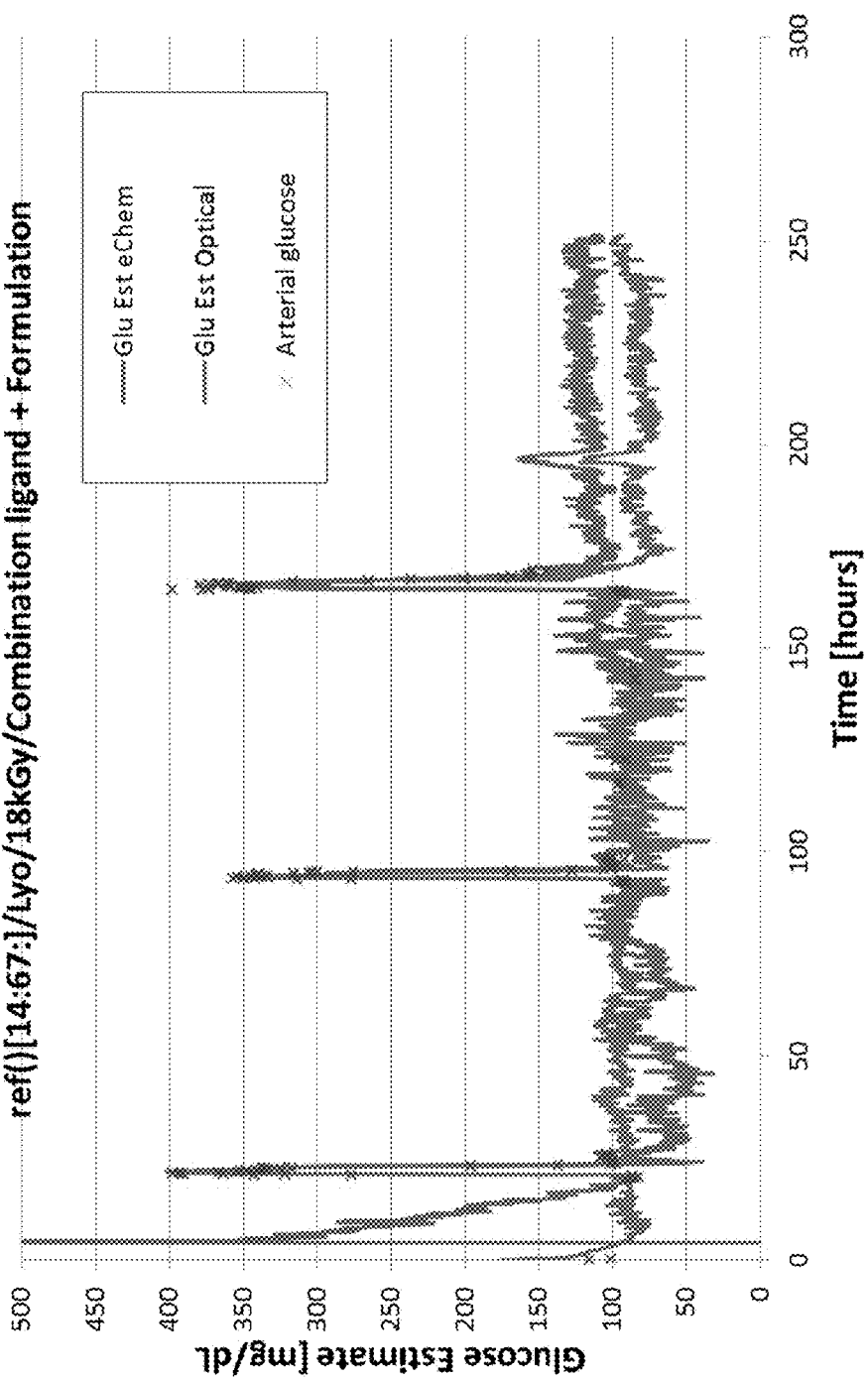
FIG. 5 is a graph illustrating data from Rat study 76: Rat #1, ORS sensor #2, in accordance with one or more embodiments of the invention. Sensor calibrated during low-high transition, first clamp.
Figure 6A:
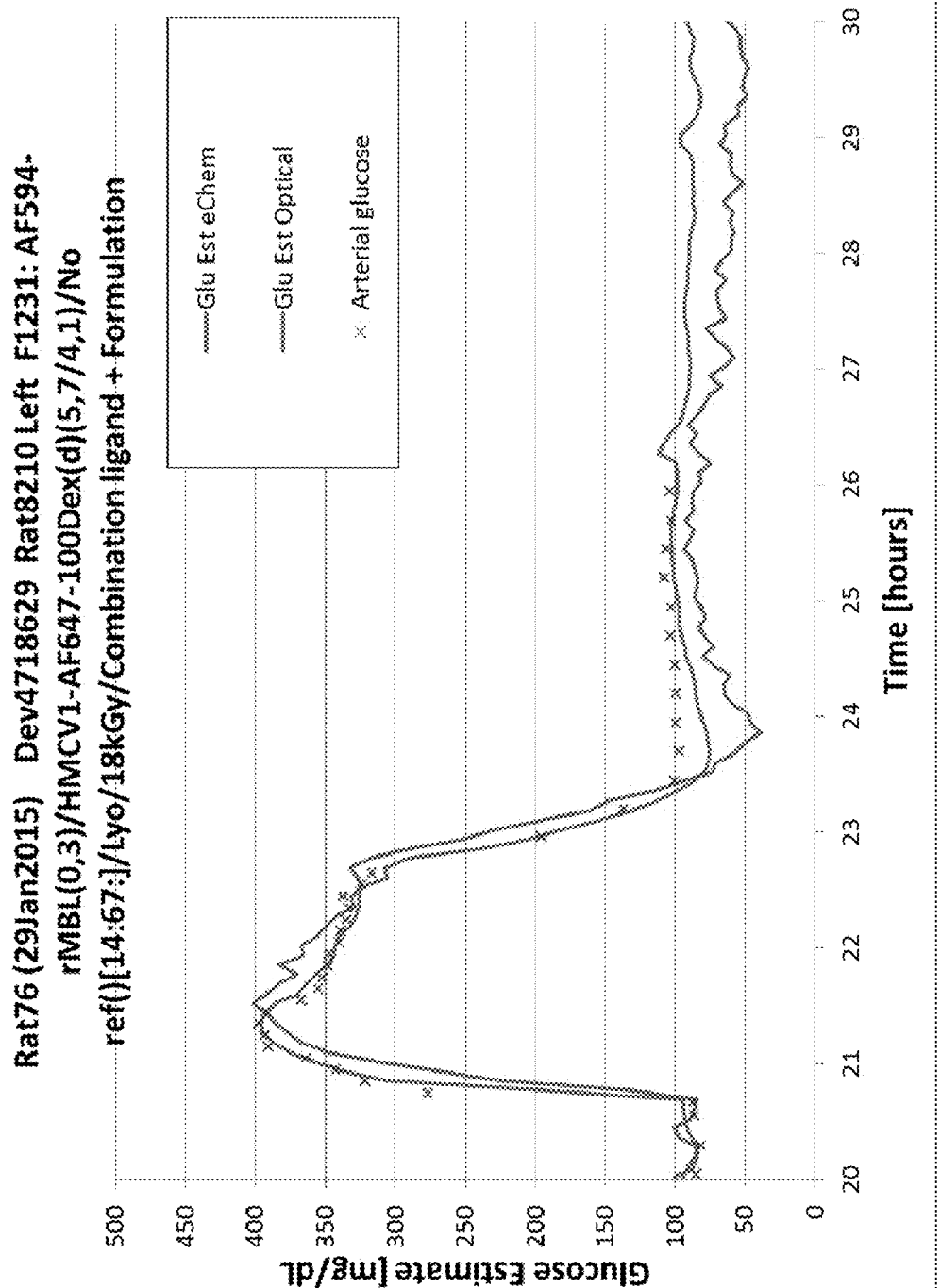
FIGS. 6A-D illustrate data from Rat study 76: Rat #1, ORS sensor #2 for clamp 1 (FIG. 6A), clamp 2 (FIG. 6B), and clamp 3 (FIG. 6C), in accordance with one or more embodiments of the invention.
Figure 6B:
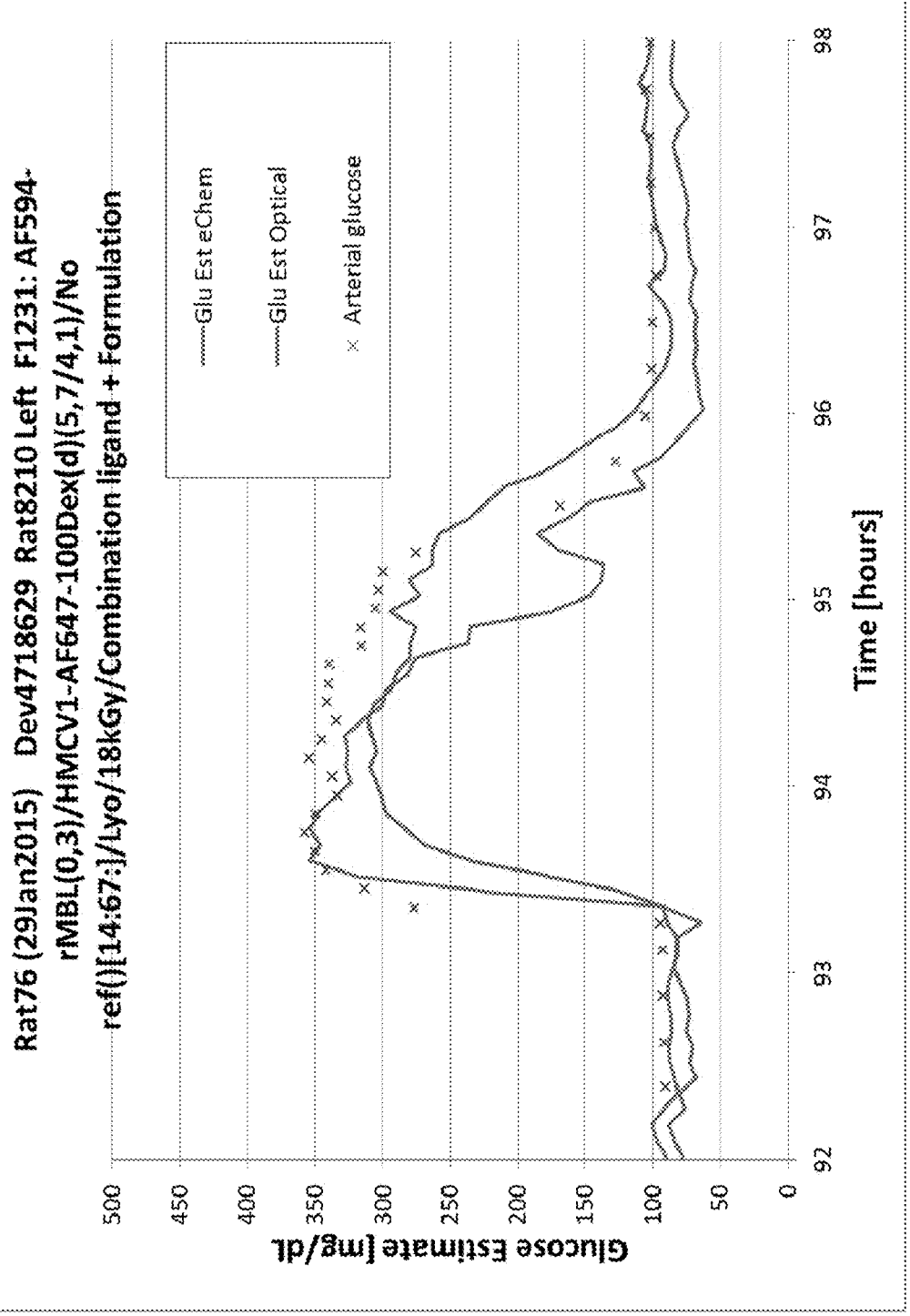
Figure 6C:
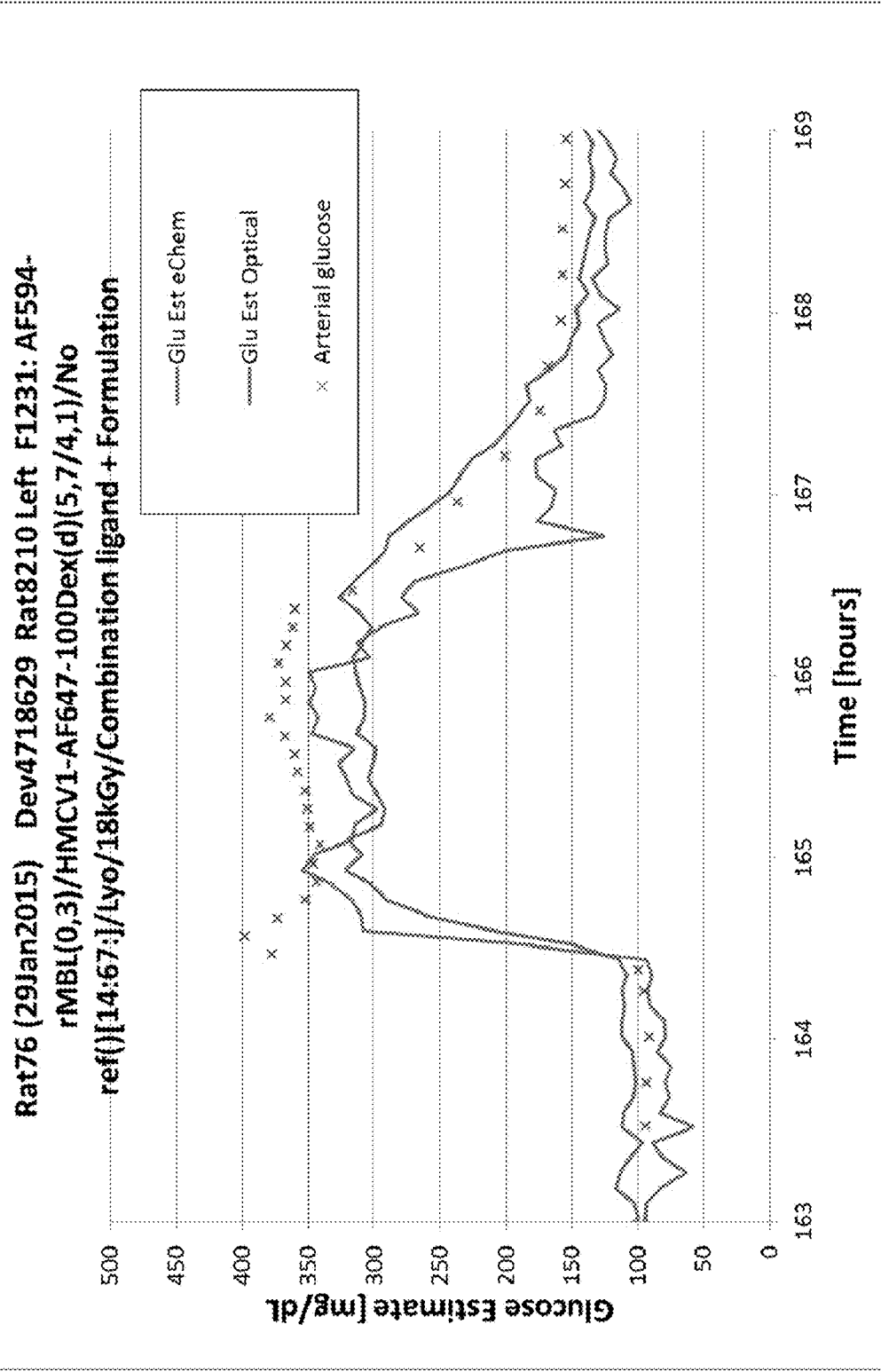
Figure 6D:
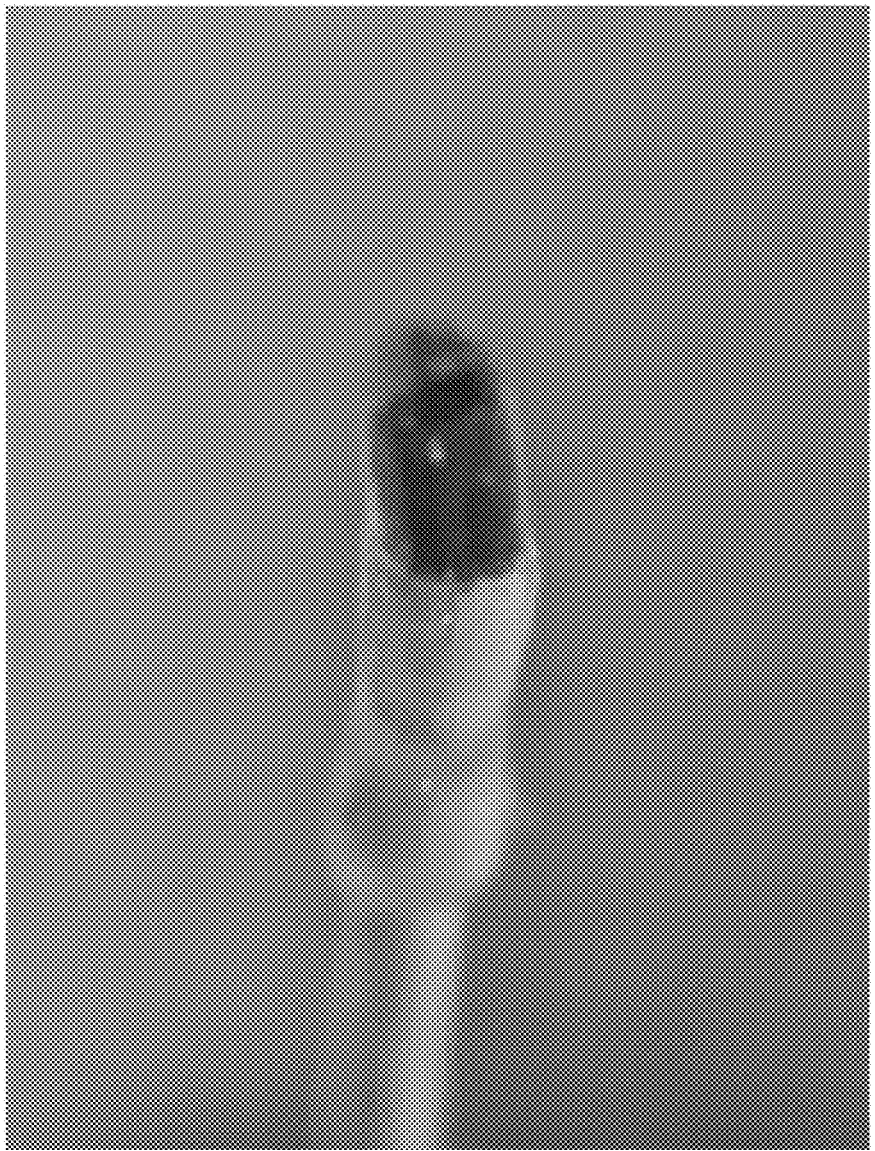
Figure 7A:
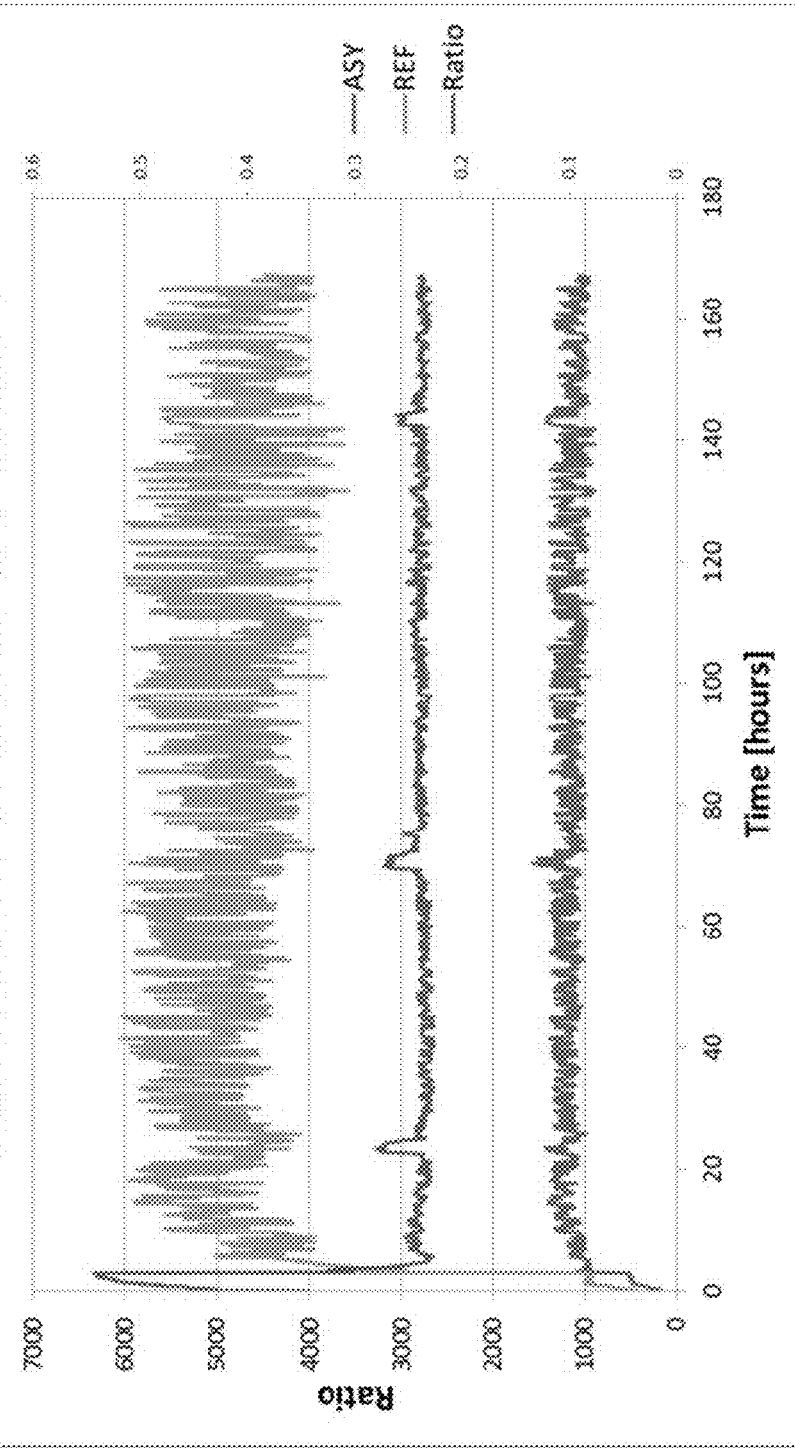
FIGS. 7A-B illustrate data from Rat study 77, in accordance with one or more embodiments of the invention.
Figure 7B:
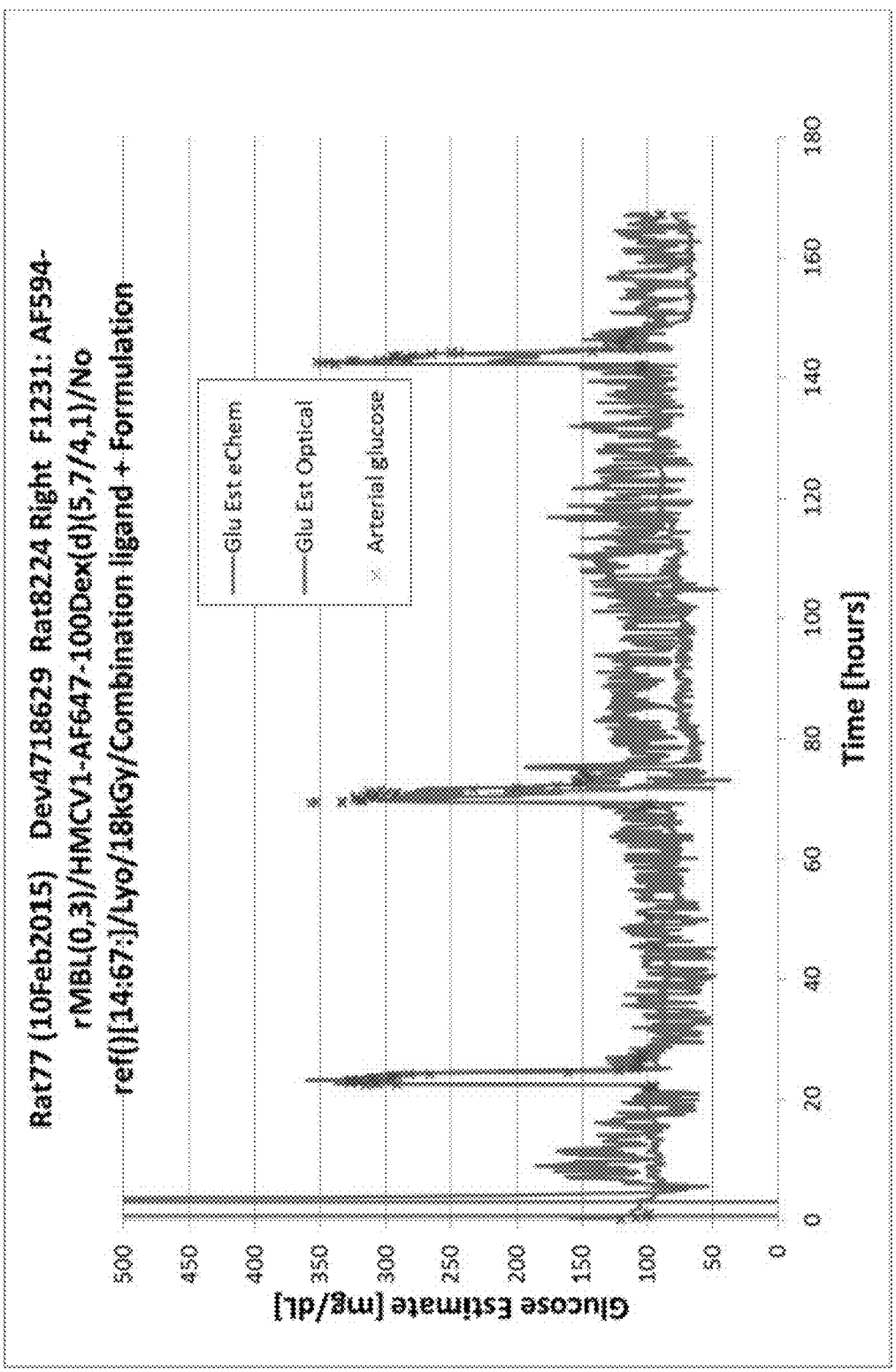
Figure 8:
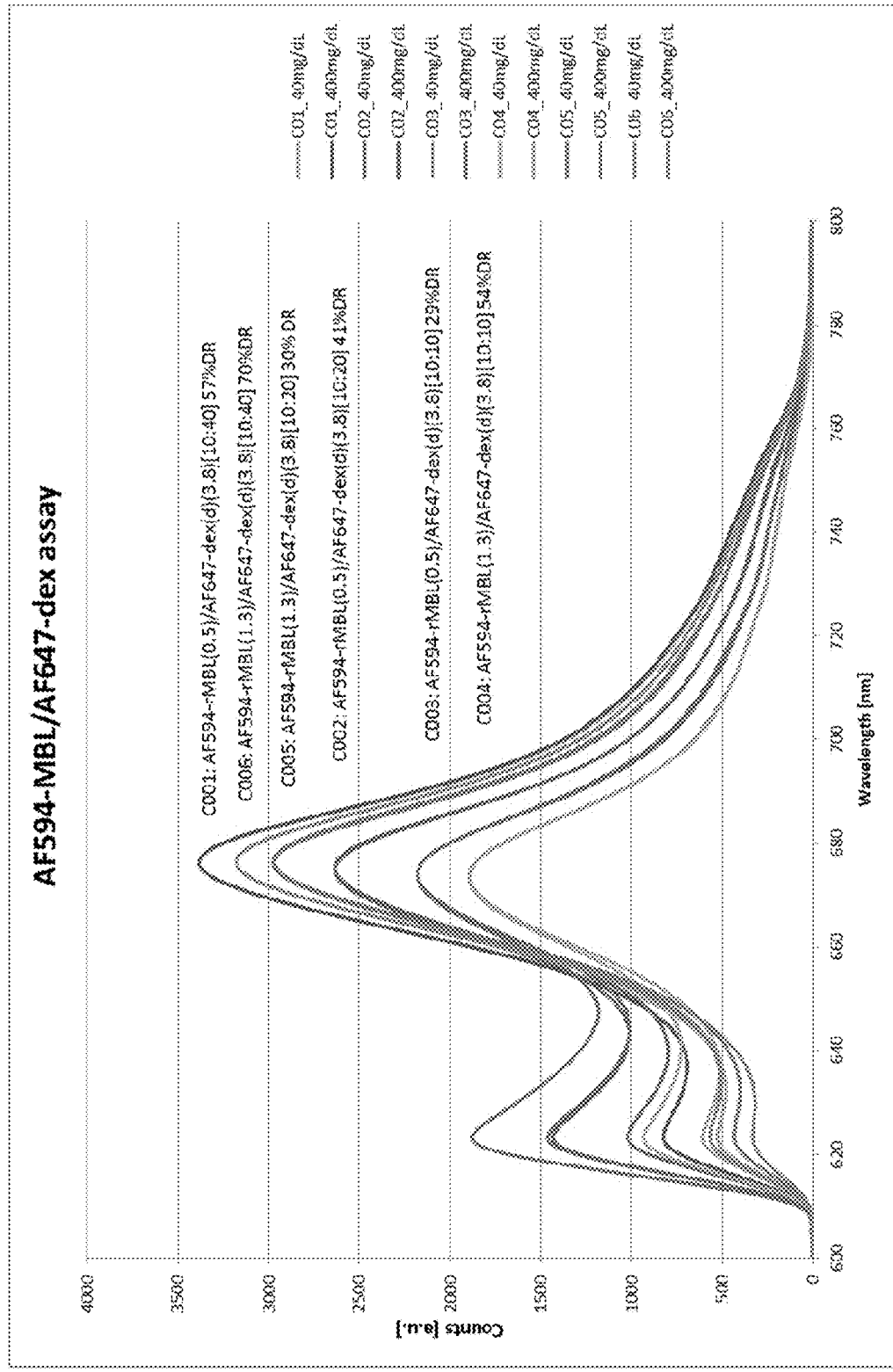
FIG. 8 is a graph illustrating data from an AF594/AF647 assay, in accordance with one or more embodiments of the invention.
Figure 9:
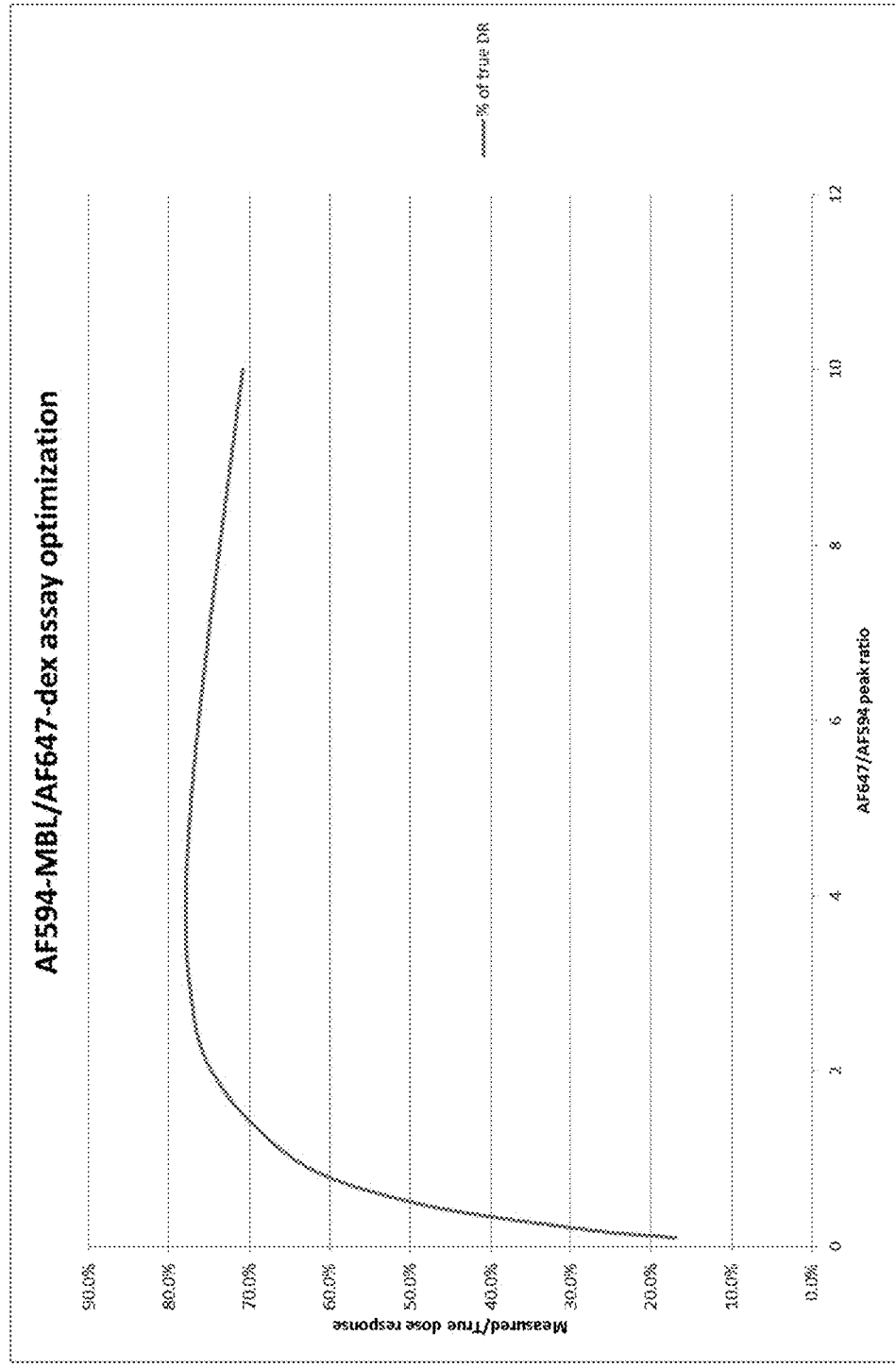
FIG. 9 is a graph illustrating data from AF594MBL/AF647-Dex and AF594/AF647-HMCV1-Dex assays: optimum ratio between AF594 and AF647 fluorescence, in accordance with one or more embodiments of the invention.
Figure 10:
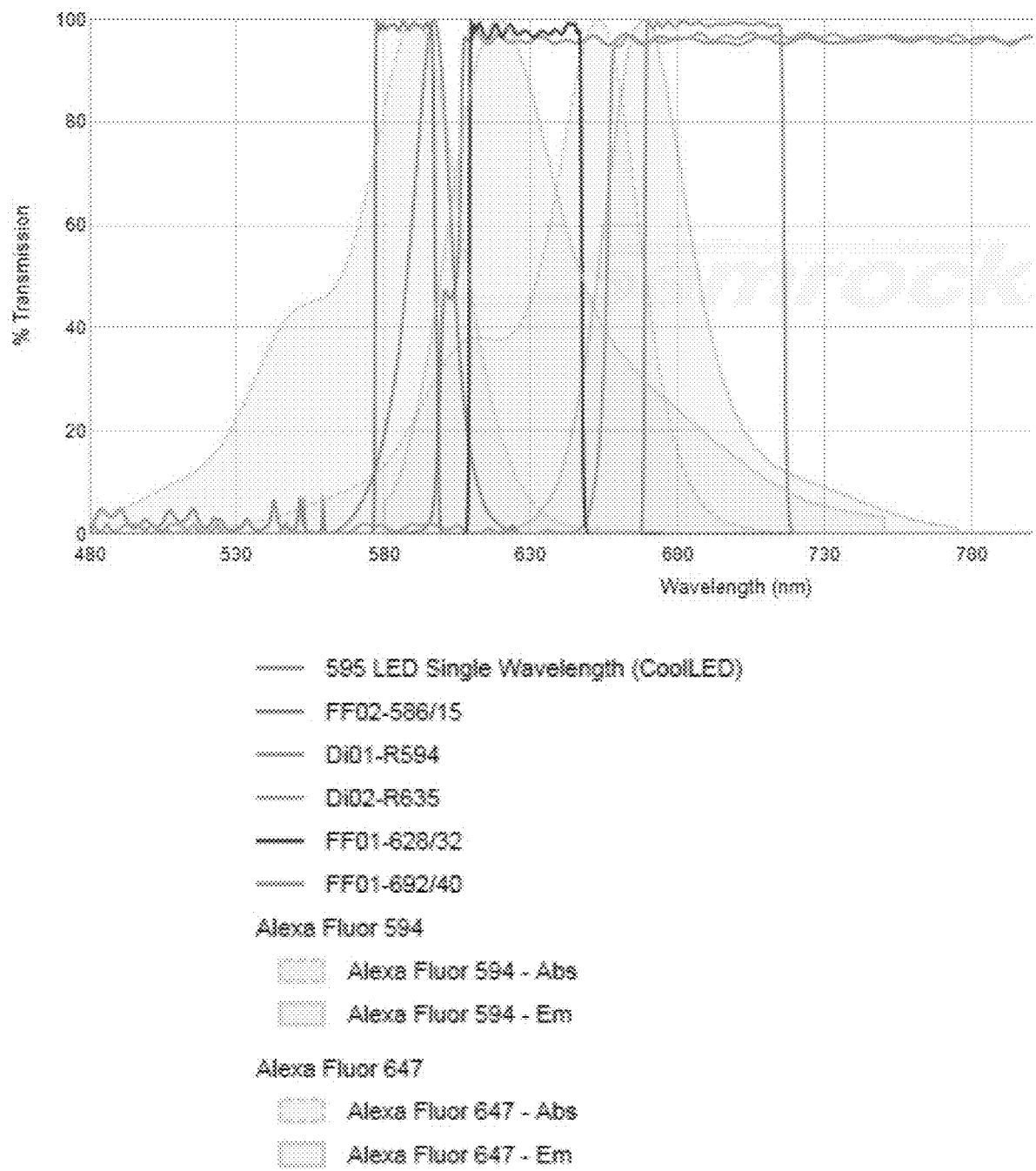
FIG. 10 is a graph illustrating data from filter configuration for AF594-MBL/647-Dex and AF594-MBL/AF647-HMCV1-Dex assays, in accordance with one or more embodiments of the invention.
Figure 11:
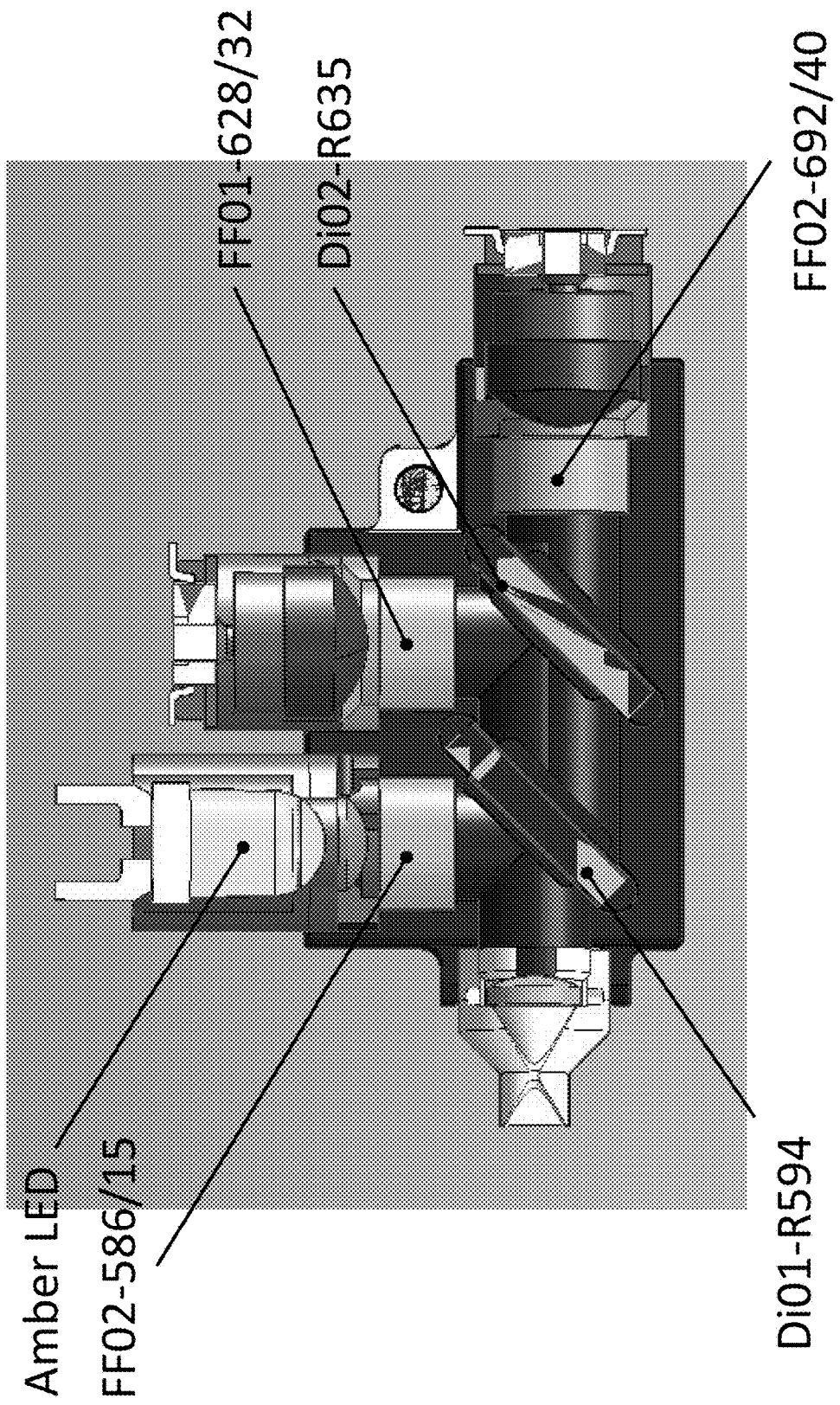
FIG. 11 illustrates the filter configuration for an AF594/647 assay, in accordance with one or more embodiments of the invention.
Figure 12A:
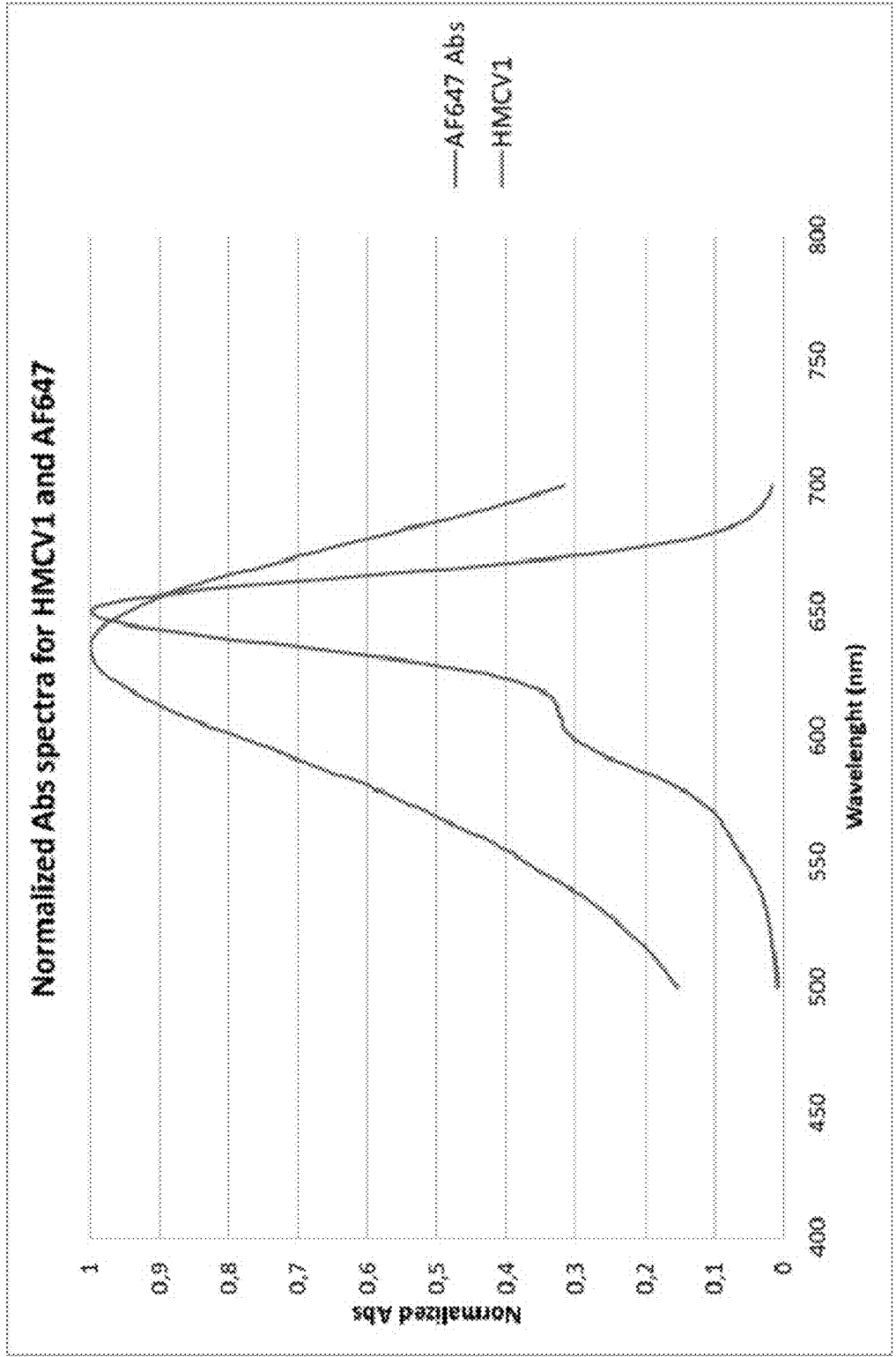
FIGS. 12A-C provide examples of degree of labeling (DOL) determination for multi-labeled dextran (MLD), in accordance with one or more embodiments of the invention.
Figure 12B:
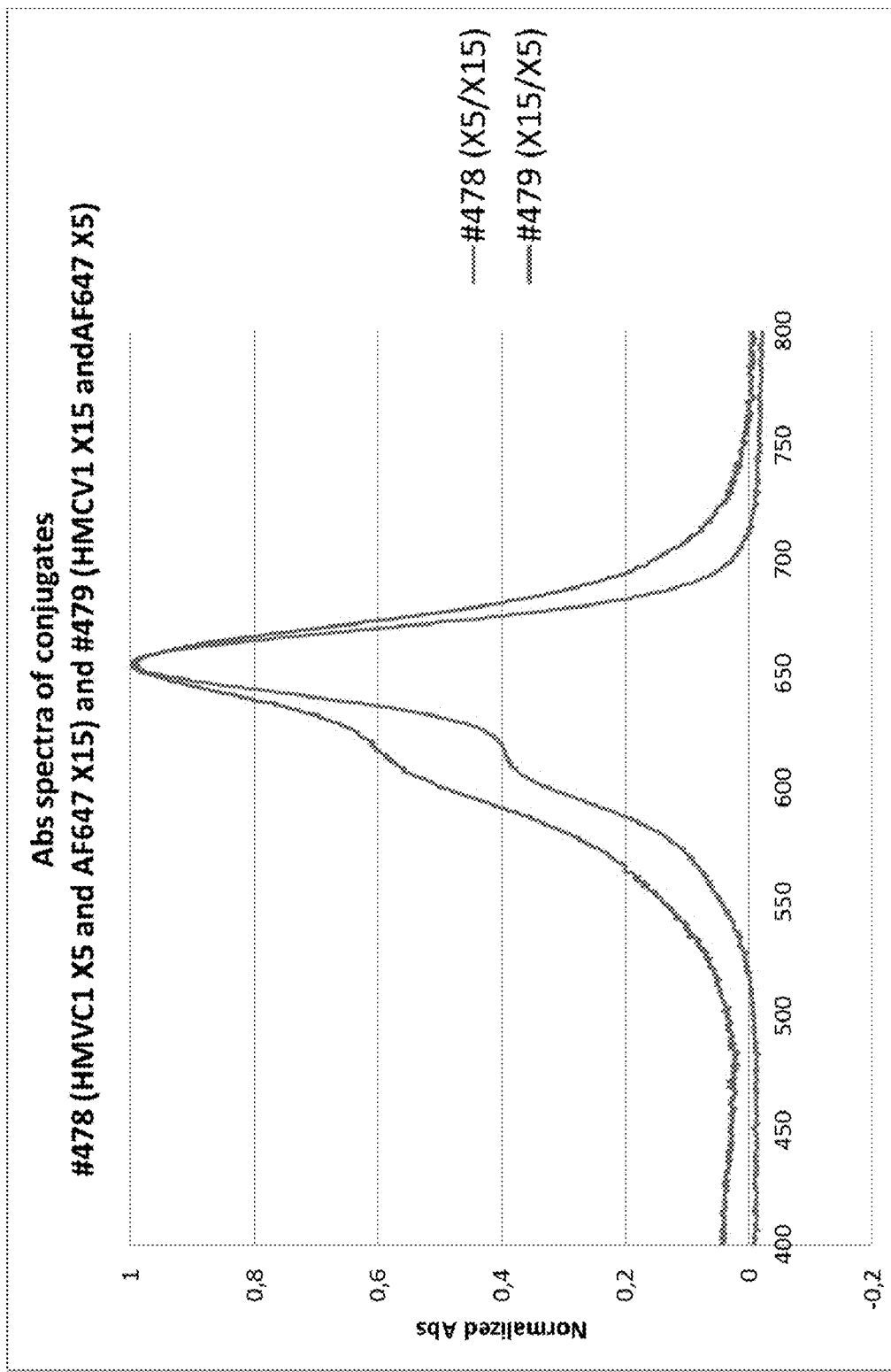
Figure 12C:
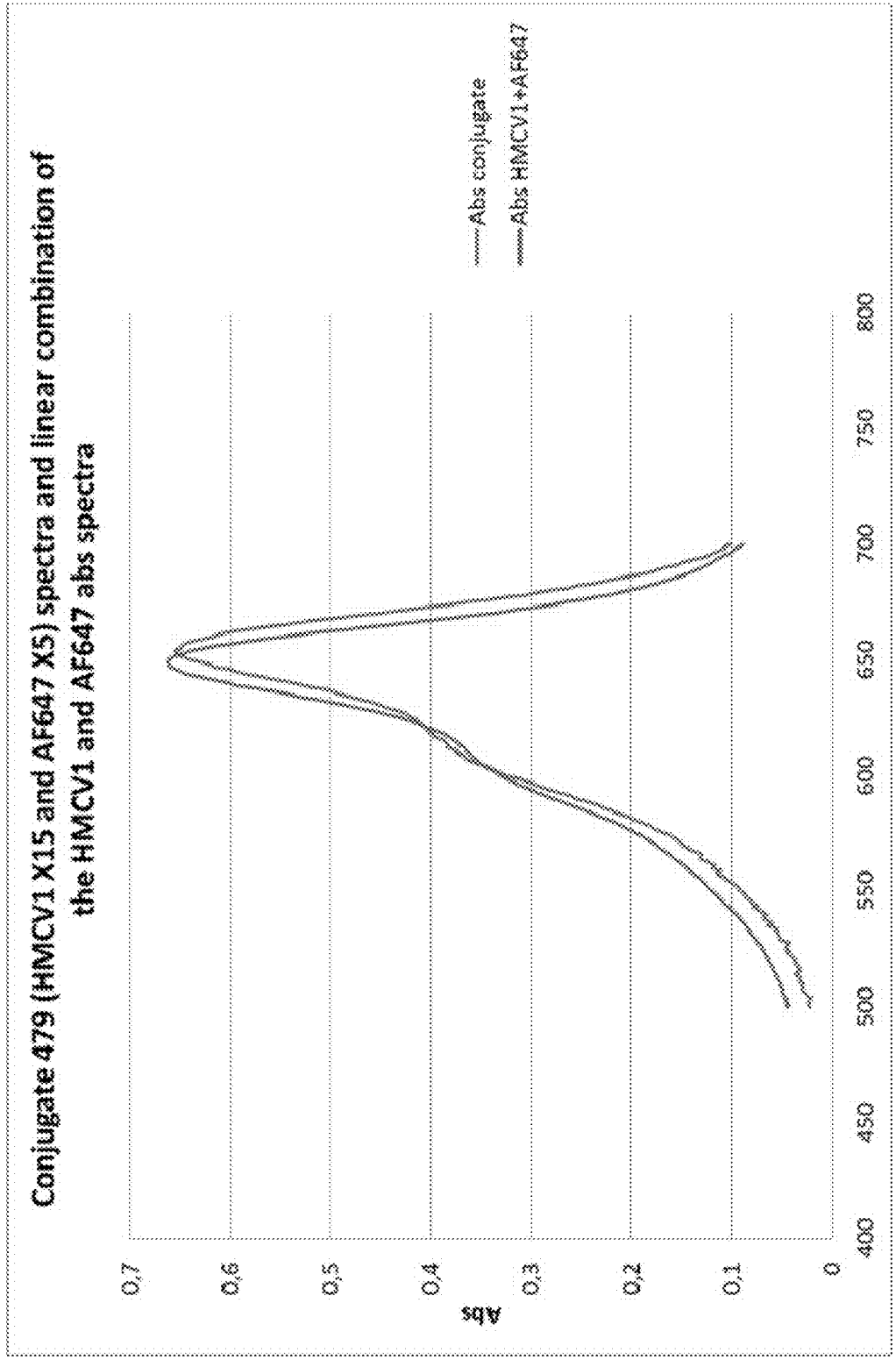
Figure 13:
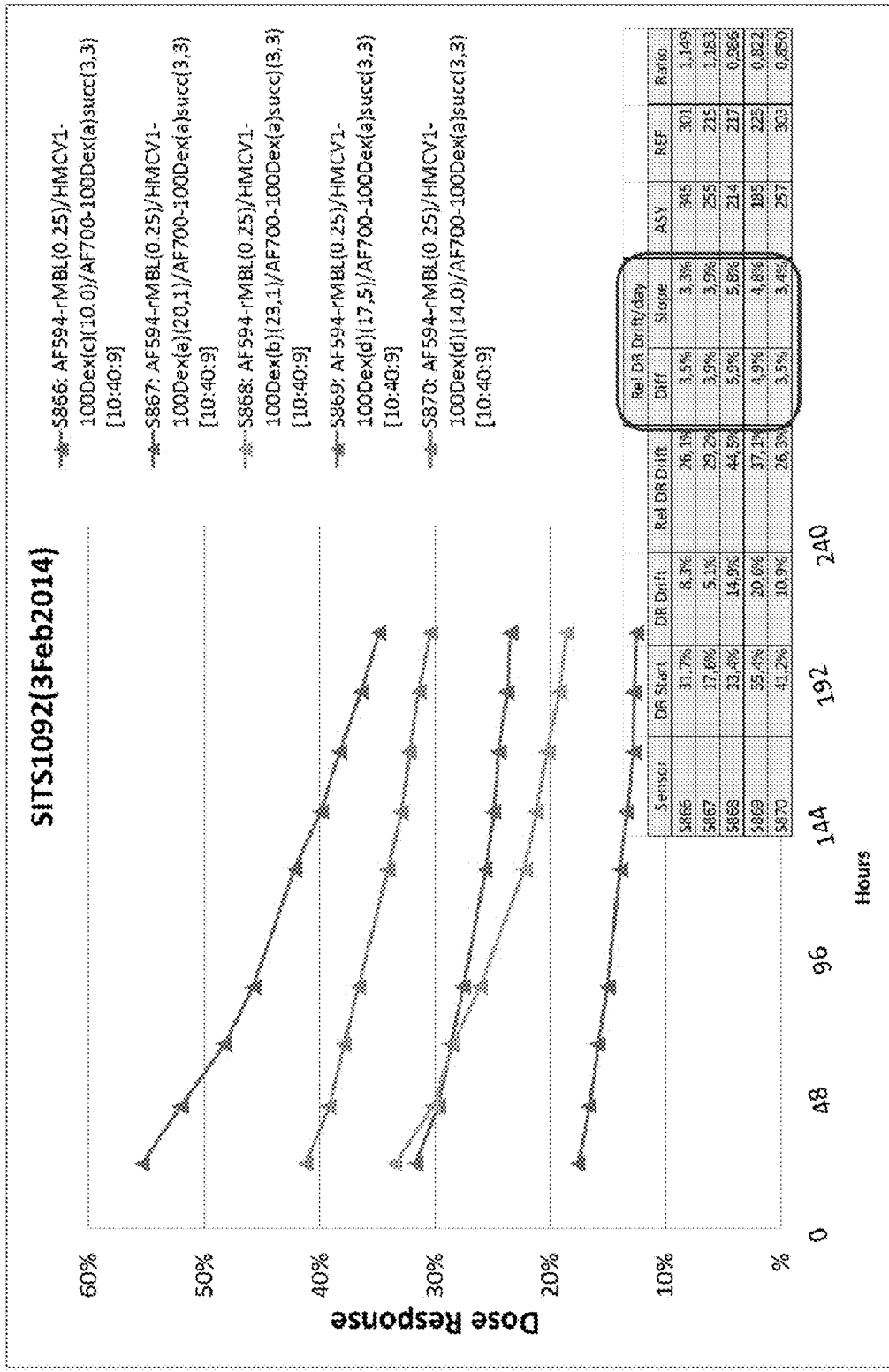
FIG. 13 is a graph illustrating single-labeled dextran performance, in accordance with one or more embodiments of the invention. The graph shows Dose Response (DR) development for five groups of sensors all build using a single labeled dextran in the glucose responding assay. DR is calculated as the difference between the normalized intensity at 400 mg/dL glucose and 40 mg/dL glucose relative to the normalized intensity at 40 mg/dL glucose. The DR loss relative to the start DR is between 3% to 6% per day. Dextrans labeled with HMCV1 only exhibits large Dose Response (DR) loss.
Figure 14:
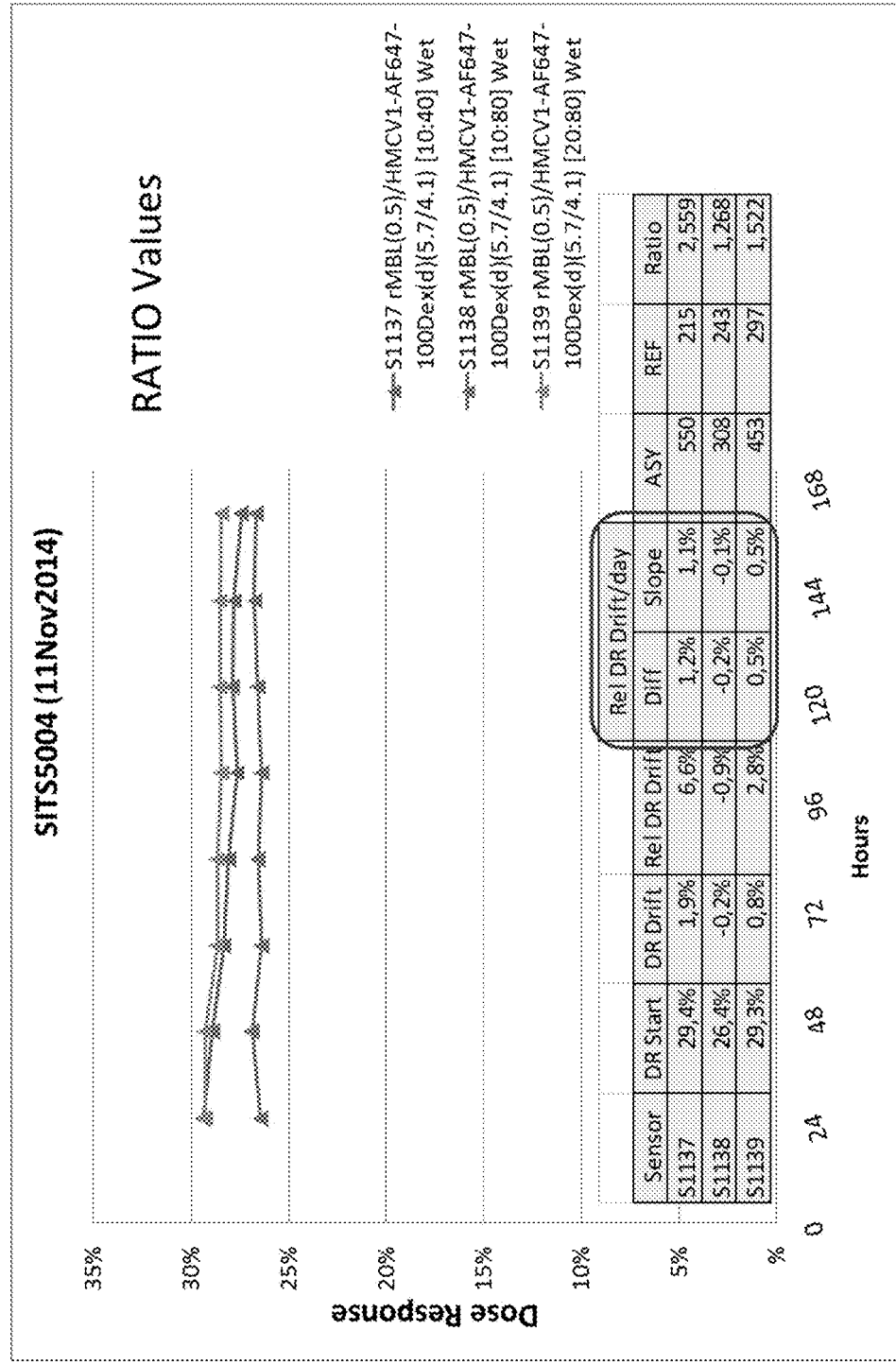
FIG. 14 is a graph illustrating multi-labeled dextran performance HMCV1-AF647-Dextran, in accordance with one or more embodiments of the invention.
Figure 15:
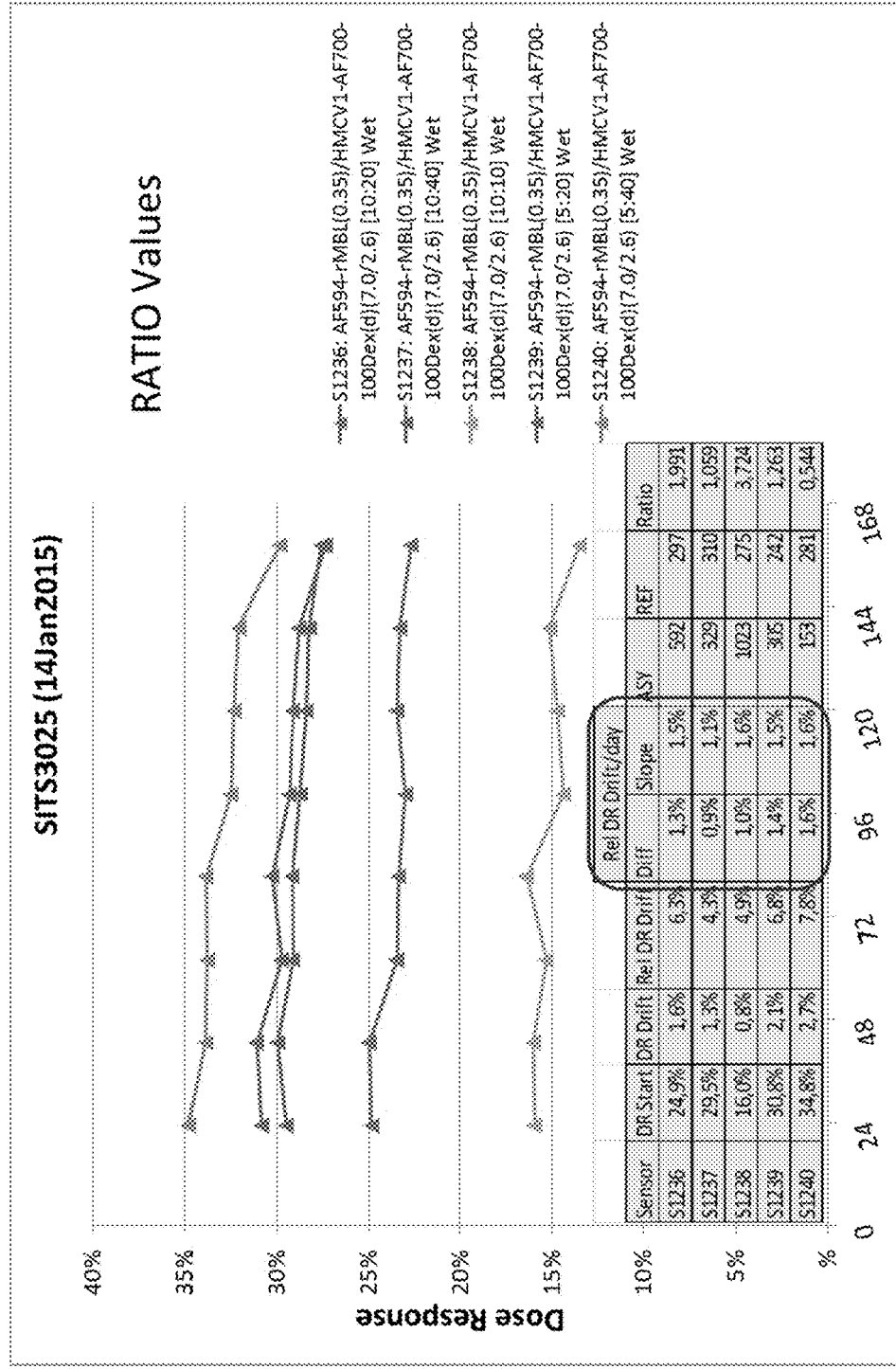
FIG. 15 is a graph illustrating multi-labeled dextran performance HMCV1-AF700-Dextran, in accordance with one or more embodiments of the invention.
Figure 16:
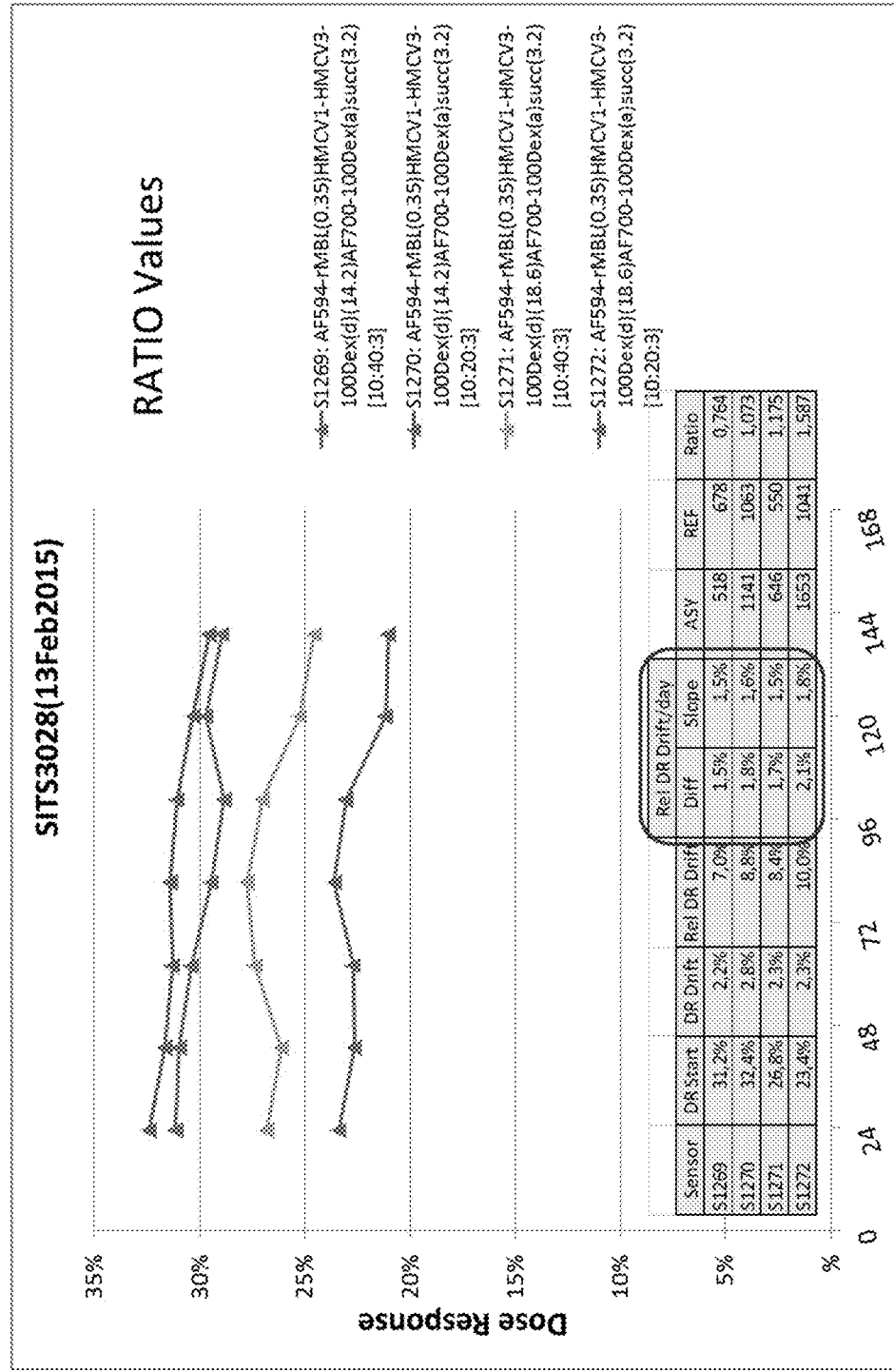
FIG. 16 is a graph illustrating multi-labeled dextran performance HMCV1-HMCV3-Dextran, in accordance with one or more embodiments of the invention.
Figure 17:
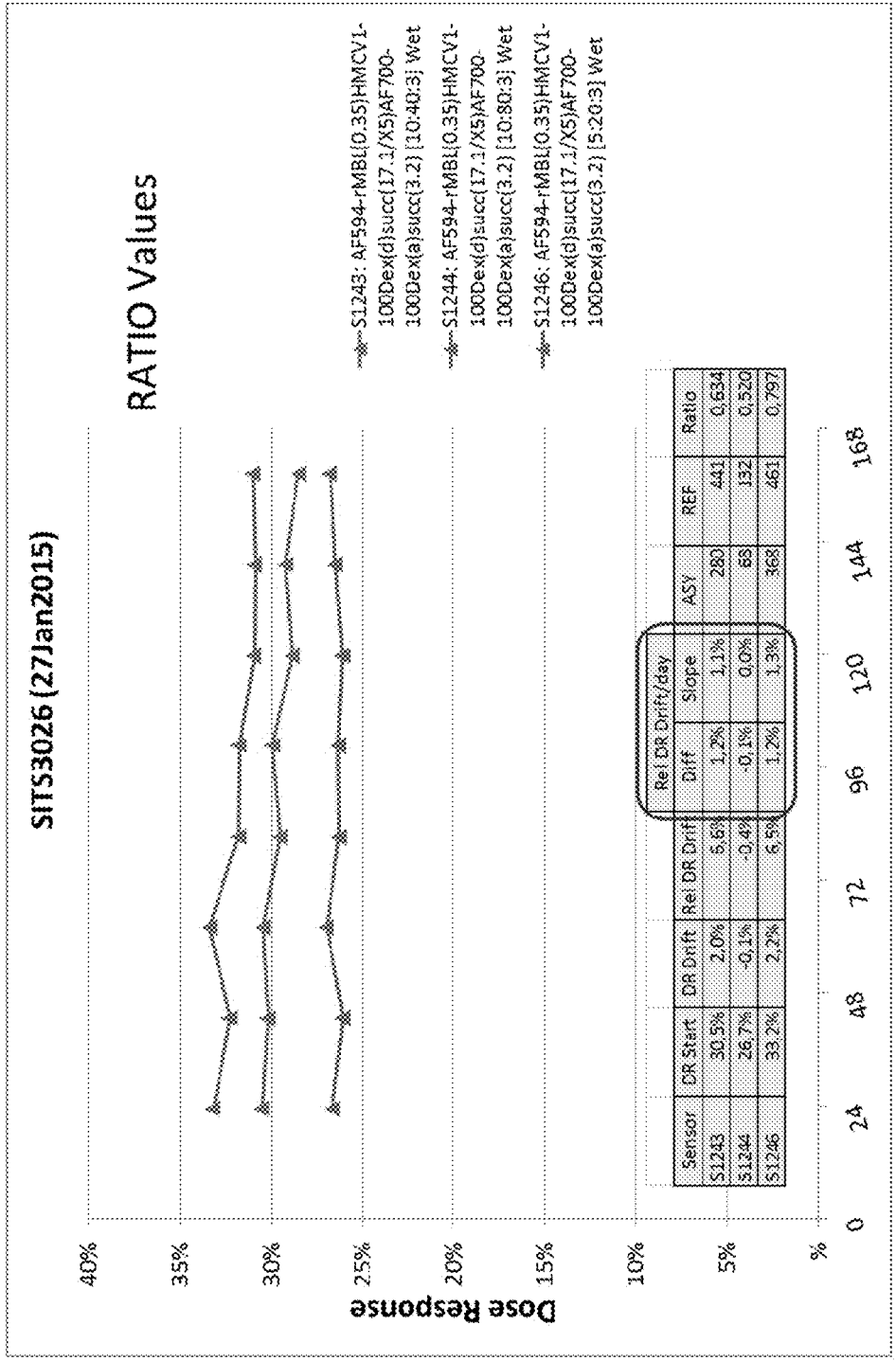
FIG. 17 is a graph illustrating multi-labeled dextran performance HMCV1-Dextran succinylated, in accordance with one or more embodiments of the invention.
Figure 18:
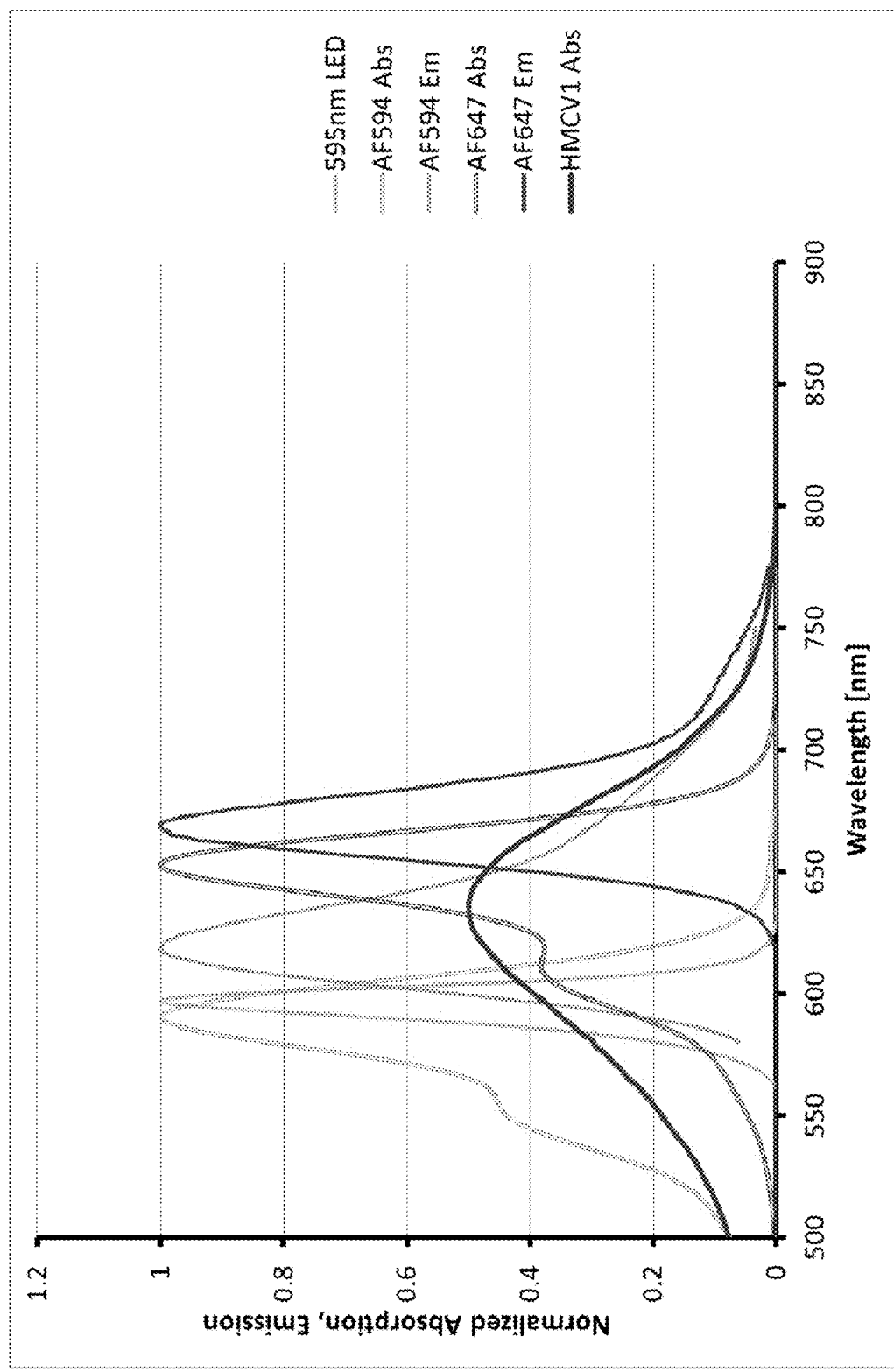
FIG. 18 is a graph illustrating normalized absorption and emission spectra of different dyes and fluorophores in a capsule sensor, in accordance with one or more embodiments of the invention.

In another embodiment, as shown in FIG. 2A, the reference fluorophore is labeled/coupled onto the same ligand as the dye quencher, thereby eliminating the need for a reference carrier. This improves the stability of the assay by improving the solubility of the ligand. This has shown even better stability than the fluorescing ligand. It also reduces the complexity of the assay as the AF647-labeled dextran acts as acceptor and reference at the same time. Additionally, this improves the photo stability of the assay by exciting the reference "where it absorbs more". It also enables further dose response optimization.

It has been found that when using a ligand labeled with only a fluorophore (e.g. AF647-100Dex(d)), increasing (AF647-100Dex(d)) concentration in the assay results in higher reference (REF) signal (risk of saturating REF) and more bleed-over into the assay (ASY) channel, which reduces sensor dose response (DR). There is a limit to (dex) concentration and the degree of labeling (DOL) of the pure AF647 ligand due to the above issues. High DOL HMCV1-dex has problems with solubility and AF647-dex appears more soluble in Tris or water. Adding HCMV1 to an AF647 ligand lowers the REF signal and bleed-over without reducing the quenching ability. Adding AF647 to an HMCV1 ligand increases solubility. Thus, specific embodiments of the invention provide adding AF647 to the HMCV1-dextran, thereby forming an AF647-HMCV1-Dex ligand with improved solubility, which improves assay stability. AF647 may be substituted with AF700. The combination ligand as well as just a HMCV1-Dex ligand may be slightly succinylated to further improve assay stability.

In another aspect of the invention, a method is provided for making the multi-labeled/combination glucose analog/ligand. In typical embodiments, the combination ligand is a dextran that carries both a quencher dye and a fluorophore, for example both HMCV1 and AF647. The two dyes are stained simultaneously to the dextran. In one instance, 10× of HMCV1-SE and 10× of AF647-SE are added to 100Dex (d). This is typically followed with purification, dialysis or passing through a small gel permeation chromatography (GPC) column.

The degree of labeling (DOL) of the individual dyes on a multi-labeled dextran (MLD) is determined by UV-Vis spectroscopy. The DOL is varied for both dyes to get a best fit. The resulting spectrum $\bar{A}(\lambda)$ from the two dyes on the dextran is a linear combination of the spectra of the individual dyes $\bar{\varepsilon}_{Dye1}(\lambda)$ and $\bar{\varepsilon}_{Dye2}(\lambda)$ and the respective dye concentration (Dyex). The dye concentration is determined by solving the equation below for all $\lambda$ in the three recorded spectra (using HMCV1 and AF647 as example).

$$\bar{A}(\lambda) = \bar{\varepsilon}_{HMCV1}(\lambda) \times [\text{HMCV1}] \times d + \bar{\varepsilon}_{AF647}(\lambda) \times [\text{AF647}] \times d$$

$$\bar{A}(\lambda) = \bar{\varepsilon}_{HMCV1}(\lambda) \times [\text{Dex}] \times \text{DOL}_{HMCV1} \times d + \bar{\varepsilon}_{AF647}(\lambda) \times [\text{Dex}] \times \text{DOL}_{AF647} \times d$$

$$\varepsilon_{HMCV1}(\lambda_{max}) = 42000 \text{ M}^{-1}\text{cm}^{-1}$$

$$\varepsilon_{AF647}(\lambda_{max}) = 270000 \text{ M}^{-1}\text{cm}^{-1}$$

As a performance evaluation of the sensors, a sensor dose response (DR) is calculated using the following equation:

$$DR = \frac{I_{400} - I_{40}}{I_{40}} \times 100\%$$

where $I_{400}$ and $I_{40}$ are the normalized intensities at 400 mg/dL and 40 mg/dL glucose. The loss in sensor dose response (DR loss) is calculated using the following equation:

$$\text{Relative Loss per day (Diff)} = \frac{DR_{Start} - DR_{end}}{DR_{Start} \times (t_{start} - t_{end})} \times 100\%$$

or from a linear regression of the DR vs. time (Excel function slope):

$$\text{Relative Loss per day (Slope)} = (-1) * \frac{\text{Slope}(DR(\text{time})_i\text{Time})}{DR_{Start}} \times 100\%$$

The relative DR loss is used as a key parameter in evaluating the quality of the sensor. Historically, the term was DR loss and hence a negative development in the DR turns out to be a positive loss, hence the (−1) multiplication in the "slope" formula. Baseline drift is evaluated but drifts much less. In illustrative experiments, as shown in FIGS. 13-17, single-labeled dextran exhibits relative DR loss between 3% to 6% per day, whereas the multi-labeled-dextran surprisingly only drifts between 0.5% and 2.5%.

Blue-Shifted Reference Dye

Embodiments of the invention include group different fluorescent dyes (e.g. a reference fluorophore and an assay fluorophore) that are selected to for use together due to their wave length profiles. Reference dyes in (intensity) fluorescence assays are needed in order to keep track of variations in the experimental setup e.g. light source fluctuations, changes in the optical path (coupling light into light guides, mechanical perturbations like bending, temperature variations, etc.). Traditionally optical or fluorescence based sensing systems have chosen references fluorophore that are red-shifted relative to the assaying fluorophore. Exciting fluorophores using light of a lower wavelength with more energy than needed there is an increased risk that the electronic transition in the fluorescent molecule will occur from the electronic ground state (S0) to the second excited state (S2) and not to the first excited electronic state (S1). Molecules in S2 are much more likely to decompose than the same molecule in S1, hence if excited to S2 faster photobleaching is obtained than if only S1 got occupied. Since a reference dye has to be very stable, the use of a reference fluorophore red-shifted relative to the assay fluorophore can be a suboptimal choice.

Instead of the usual red-shifted reference fluorophore that could appear photo-labile due to low wavelength excitation, certain embodiments of the invention use a reference fluorophore blue-shifted relative to the assay or indicator fluorophore instead. In other words, the reference fluorophore has a shorter wavelength/increased frequency than the assay fluorophore. In visible light, the reference fluorophore is closer to the blue end of the spectrum whereas the assay fluorophore is closer to the red end. This improves the stability of the reference fluorophore, which is a key property in providing accurate assay measurements. In one or more embodiments, a competitive glucose binding affinity assay comprises a glucose receptor/lectin (e.g. mannan binding lectin) labeled with an assay fluorophore (Alexa Fluor™ 647) and a multi-labeled glucose analog (e.g. dextran) labeled with both a reference fluorophore (e.g. Alexa Fluor™ 594) and a quencher dye (e.g. hexamethoxy crystal violet-1), wherein the reference fluorophore is blue-shifted relative to the assay fluorophore.

As is known in the art, with such systems, spectra and available light sources dictate the selection of the fluorophores and the design of the optical set-up. There are a variety of semiconductor light sources (LED's) useful with embodiments of the invention such as those found in the MIGHTEX SYSTEMS LED Wavelength Portfolio. In addition, in embodiments of the invention, continuum light sources (white light sources with laser characteristics) can be filtered to select a particular wavelength range for excitation to provide an arbitrary wavelength(range)

Typically, for a red-shifted reference the concentration of the reference can in principle be increased to reduce the effect of the assay fluorophore "red" tail bleed over and must be separated approximately 50 nm to avoid reference fluorophore "blue" tail bleed over to the assay fluorophore and thereby reduce dose response. For a blue-shifted reference the fluorophore must typically be blue-shifted approximately 50 nm to avoid reference assay "blue" tail bleed over to the reference fluorophore and thereby make the reference insensitive to assay fluorophore fluorescence level. Reference fluorophore concentrations can in this case be reduced in order to avoid dose response reduction by reference "red" tail bleed into the assay fluorophore emission. For most fluorophore pairs, it is typically difficult to separate fluorophores more than 100 nm and still be able to excite the most red-shifted fluorophore simultaneously with the blue-shifted. One way to circumvent this is to excite with two different light sources, and increase the complexity of the optical system as it is required to monitor the output of the light sources to compensate for changes in output.

Nomenclature

As described herein and in the figures, the different dextran conjugates have the following general nomenclature:

Dye1-Dye2-XXXDex(Y)succ(a/b/Xc)

As described herein and in the figures, the different MBL conjugates have the following general nomenclature:

Dye1-zMBL(a)

Dye1 and Dye2 are abbreviations of the dye names;

XXX is the Mw of the dextran in kDa;

Y is the Ion Exchange Chromatography (IEX) fraction of the amino-dextran;

Z is either "r" for recombinant MBL, "p" for plasma MBL, "UHP" for Ultra Highly Purified MBL;

succ denotes if the dextran is treated with succinic acid anhydride in molar excess "c". If succ is not stated the dextran is stained with dye(s) only; and (a/b/Xc) denotes the Degree Of Labeling (DOL) of the dyes and excess of succinic acid anhydride used. "a" is the DOL of Dye1, "b" is the DOL or Dye2 and "Xc" the molar excess of succinic acid anhydride used. DOL is defined as number of dyes per dextran i.e. a dimensionless number.

Illustrative examples are as follows:

HMCV1-AF647-100Dex(d)(5.2/3.9)

This conjugate is a 100 kDa Dextran IEX peak-d labeled with HMCV1 and AF647 and having respectively DOLs of 5.2 and 3.9.

HMCV1-100Dex(c)succ(12.1/X10)

This conjugate is a 100 kDa Dextran IEX peak-c labeled with HMCV1 and succinic acid anhydride having DOL of 12.1 and 10 times molar excess of succinic acid anhydride used for modification.

AF647-rMBL(0.51)

This conjugate is recombinant MBL labeled with AF647 having DOL of 0.51.

Assays are described as MBL and ref-conjugates (when needed) from the same nomenclature and the concentrations of the individual conjugates in square brackets (PP;DD;RR) where PP is the concentration of MBL (rMBL) in µM, DD is the ligand dextran concentration (Dex) in µM and RR is the reference dextran concentration in µM.

Further aspects and embodiments of the invention are disclosed in the following examples.

EXAMPLES

Example 1: Illustrative Multi-Labeled Dextrans Generated

HMCV1-AF647-Dextran

Dextran carrying both HMCV1 quencher dye and AF647 fluorophore. Both HMCV1 and AF647 acts as quencher to the AF594 donor in the glucose sensing assay. AF647 also functions as reference in the system. The emitted fluorescence from the direct excitation from the light source is much larger than the glucose dependent fluorescence origin from the FRET in the system.

HMCV1-AF700-Dextran

Dextran carrying both HMCV1 quencher dye and AF700 fluorophore. HMCV1 acts as quencher to the AF594 donor in the glucose sensing assay. AF700 functions as reference in the system.

HMCV1-HMCV3-Dextran

Dextran carrying both HMCV1 quencher dye and HMCV3 quencher dye. HMCV3 is a negatively charged version of HMCV1 (that is positively charged). Both HMCV1 and HMCV3 acts a quencher to the AF594 donor in the glucose sensing assay. A reference is needed in the system e.g. heavily succinylated AF700-Dextran.

HMCV1-Dextran-succinlylated

Dextran carrying HMCV1 quencher dye and further treated low excess succinic acid anhydride. HMCV1 acts as quencher to the AF594 donor in the glucose sensing assay. The low degree of succinylation prevents the dextran from fast obtaining a lipophilic structure. A reference is needed in the system e.g. heavily succinylated AF700-Dextran.

Example 2: Experiment with Blue-Shifted Reference Fluorophore

In the glucose responding assay, the assay has traditionally been built from two or three conjugates. Option 1 (three ligands) using red-shifted reference: AF594-rMBL, HMCV1-100Dex(d), AF700-100Dex(a)succ; AF700 on the non-binding Dex(a)succ acts as a reference. Option 2 (two ligands) using red-shifted reference: AF594-rMBL, HMCV1-AF647-100Dex(d); AF647 on the binding Dex(d) will act a reference since the fluorescence from direct excitation is much stronger than the fluorescence originating from the FRET. Changing the system to a blue-shifted reference becomes: AF647-rMBL and HMCV1-AF594-100Dex(d), resulting in better stability and lower calibration frequency of the optical sensor.

The assay was been built but unfortunately the AF594-DOL of the HMCV1-AF594-100Dex(d)(6.0/6.3) was far too large (SITS6017). This resulted in full saturation in both the REF and ASY channel during testing. New assays were made, but not tested (closing of site). Option 1: AF647-rMBL(0.24)/HMCV1-100Dex(d)succ(17.1/X5)/AF594-100Dex(a)succ(2.0); (10:40:1) and (10:40:0.5). Option 2: AF647-rMBL(0.24)/HMCV1-70 Dex(d)succ(13.8/X5)/AF594-100Dex(a)succ(2.0) (10:40:1) and (10:80:1). Option 3: AF647-rMBL(0.24)/HMCV1-HMCV3-100Dex(d)succ(14.2)/AF594-100Dex(a)succ(2.0) (10:40:1) and (10:40:0.1); AF647-rMBL(0.24)/HMCV1-HMCV3-100Dex(d)succ(18.6)/AF594-100Dex(a)succ(2.0) (10:40:1) and (10:40:0.1).

CONCLUSION

This concludes the description of the typical embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A glucose sensing complex comprising:
mannan binding ligand, wherein the mannan binding ligand is coupled to an assay fluorophore;
a reference fluorophore;
dextran, wherein the dextran functions in the assay as a glucose analog and is coupled to:
the reference fluorophore;
an agent that enhances the hydrophilicity of the dextran;
a quenching agent, wherein the assay fluorophore and quenching agent form a Förster Resonance Energy Transfer (FRET) pair; and
the glucose sensing assay complex exhibits a sensor dose response (DR) loss of less than 2.5% per day.

2. The glucose sensing complex of claim 1 wherein the agent that enhances the hydrophilicity of the dextran is the quenching agent.

3. The glucose sensing complex of claim 2 wherein the quenching agent is hexamethoxy crystal violet-1 (HMCV1).

4. The glucose sensing complex of claim 1 wherein the reference fluorophore is Alexa Fluor 647 (AF647) or Alexa Fluor 700 (AF700).

5. The glucose sensing complex of claim 1 wherein the fluorophores and/or quenching agent are water soluble.

6. The glucose sensing complex of claim 1 wherein the dextran is modified by an anhydride compound.

7. The glucose sensing complex of claim 1 wherein the dextran comprises less than 1500 glucose units.

8. The glucose sensing complex of claim 1 wherein the Degree of Labeling (DOL) of the fluorophore is 4.1 and the DOL of the quencher dye is 5.7.

9. The glucose sensing complex of claim 1 wherein the agent that enhances the hydrophilicity of the dextran comprises a cyclic anhydride or a tartaric anhydride derivate.

10. The glucose sensing complex of claim 1 wherein the agent that enhances the hydrophilicity of the dextran comprises a succinic acid, a glutaric acid, an adipic acid, a pimelic acid, a suberic acid, an azelaic acid or a sebacic acid.

11. A glucose sensing complex comprising:
mannan binding ligand, wherein the mannan binding ligand is coupled to an assay fluorophore;
a reference fluorophore;
dextran, wherein the dextran functions in the assay as a glucose analog and is coupled to:
the reference fluorophore;
an agent that enhances the hydrophilicity of the dextran, wherein the agent that enhances the hydrophilicity of the dextran comprises a cyclic anhydride, a tartaric anhydride derivate, a succinic acid, a glutaric acid, an adipic acid, a pimelic acid, a suberic acid, an azelaic acid or a sebacic acid; and
a quenching agent, wherein the assay fluorophore and quenching agent form a Förster Resonance Energy Transfer (FRET) pair.

12. The glucose sensing complex of claim 11, wherein the Degree of Labeling (DOL) of the fluorophore is 4.1 and the DOL of the quencher dye is 5.7.

13. The glucose sensing complex of claim 11, wherein the dextran comprises about 600 glucose units.

* * * * *